(12) United States Patent
Lin et al.

(10) Patent No.: US 7,935,342 B2
(45) Date of Patent: May 3, 2011

(54) METHODS FOR TREATING OBESITY BY ADMINISTERING A TRKB ANTAGONIST

(75) Inventors: John Chia-Yang Lin, Palo Alto, CA (US); Arnon Rosenthal, Woodside, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 0 days.

(21) Appl. No.: 12/278,182

(22) PCT Filed: Jan. 29, 2007

(86) PCT No.: PCT/IB2007/000264
§ 371 (c)(1),
(2), (4) Date: Feb. 3, 2009

(87) PCT Pub. No.: WO2007/088479
PCT Pub. Date: Aug. 9, 2007

(65) Prior Publication Data
US 2010/0008933 A1    Jan. 14, 2010

Related U.S. Application Data

(60) Provisional application No. 60/764,864, filed on Feb. 2, 2006.

(51) Int. Cl.
*A61K 39/395* (2006.01)
*A61K 39/44* (2006.01)
*A61K 39/00* (2006.01)
*A61K 38/17* (2006.01)

(52) U.S. Cl. ............... 424/139.1; 424/134.1; 514/21.2; 514/910

(58) Field of Classification Search .............. None
See application file for complete search history.

(56) References Cited

U.S. PATENT DOCUMENTS

| | | | |
|---|---|---|---|
| 3,773,919 A | 11/1973 | Boswell et al. | |
| 4,777,127 A | 10/1988 | Suni et al. | |
| 5,109,113 A | 4/1992 | Caras | |
| 5,219,740 A | 6/1993 | Miller et al. | |
| 5,240,846 A | 8/1993 | Collins | |
| 5,349,056 A | 9/1994 | Wilson | |
| 5,364,768 A | 11/1994 | Altamura et al. | |
| 5,364,769 A | 11/1994 | Rosenthal | |
| 5,422,120 A | 6/1995 | Kim | |
| 5,578,476 A | 11/1996 | Zenno et al. | |
| 5,580,859 A | 12/1996 | Felgner et al. | |
| 5,599,560 A | 2/1997 | Siuciak | |
| 5,644,034 A | 7/1997 | Rathjen et al. | |
| 5,670,488 A | 9/1997 | Gregory et al. | |
| 5,686,253 A | 11/1997 | Skold et al. | |
| 5,686,579 A | 11/1997 | Shami et al. | |
| 5,702,906 A | 12/1997 | Rosenthal | |
| 5,759,573 A | 6/1998 | Kim | |
| 5,766,627 A | 6/1998 | Sankaram | |
| 5,770,577 A | 6/1998 | Kinstler et al. | |
| 5,780,484 A | 7/1998 | Zelle et al. | |
| 5,814,482 A | 9/1998 | Dubensky, Jr. et al. | |
| 5,827,823 A | 10/1998 | Siuciak et al. | |
| 5,830,858 A | 11/1998 | Rosenthal | |
| 5,837,510 A | 11/1998 | Goldsmith | |
| 5,840,736 A | 11/1998 | Zelle et al. | |
| 5,843,453 A | 12/1998 | Holder et al. | |
| 5,925,345 A | 7/1999 | Anderson et al. | |
| 6,010,868 A | 1/2000 | Neuenhofer et al. | |
| 6,013,517 A | 1/2000 | Respess | |
| 6,024,734 A | 2/2000 | Brewitt | |
| 6,037,320 A | 3/2000 | Rosenthal | |
| 6,090,382 A | 7/2000 | Salfeld et al. | |
| 6,099,857 A | 8/2000 | Gross | |
| 6,143,537 A | 11/2000 | Kwan et al. | |
| 6,143,718 A | 11/2000 | Kolterman et al. | |
| 6,153,189 A * | 11/2000 | Presta et al. ............... | 424/134.1 |
| 6,184,360 B1 | 2/2001 | Burton et al. | |
| 6,376,471 B1 | 4/2002 | Lawrence, III et al. | |
| 6,391,312 B1 | 5/2002 | Kishino et al. | |
| 6,413,942 B1 | 7/2002 | Felqner et al. | |
| 6,436,908 B1 | 8/2002 | Koch et al. | |
| 6,472,366 B2 | 10/2002 | Kishino et al. | |
| 6,506,728 B2 | 1/2003 | Rosenthal | |
| 6,565,874 B1 | 5/2003 | Dunn et al. | |
| 6,566,091 B1 | 5/2003 | Rosenthal | |
| 6,811,774 B2 | 11/2004 | Haddada et al. | |
| 6,949,655 B2 | 9/2005 | Lauffer et al. | |
| 2002/0013351 A1 | 1/2002 | McCaffrey et al. | |
| 2002/0045576 A1 | 4/2002 | Rosenthal | |
| 2002/0111347 A1 | 8/2002 | Harbeson et al. | |

(Continued)

FOREIGN PATENT DOCUMENTS

EP    0 298654 A2    1/1989

(Continued)

OTHER PUBLICATIONS

Lin et al (2008. PLoS ONE. 3(4): 1-7).*
Cazorla et al (2010. PLoS One. 5(3): 1-17).*
Phillips, A., J Pharm Pharmacology 53: 1169-1174, 2001.*
Vidal et al. 2005. European Journal of Cancer. 41: 2812-2818.*
Pirollo et al, 2008. Cancer Res. 68(5): 1247-1250.*
Adams, G. et al. (Nov. 2003). "Targeting Cytokines to Inflammation Sites," Nature Biotechnology 21(11):1314-1320.
Andrieu, D. et al. (Dec. 2003). "Expression of the Prader-Willi Gene Necdin During Mouse Nervous System Development Correlates with Neuronal Differentiation and p75NTR Expression," *Gene Exor. Patterns* 3(6):761-765.
Apfel, S.C. (Apr. 1999). "Neurotrophic Factors in Peripheral Neuropathies: Therapeutic Implications," Brain Pathol. 9(2):393-413.

(Continued)

*Primary Examiner* — Bridget E Bunner
*Assistant Examiner* — Zachary C Howard
(74) *Attorney, Agent, or Firm* — Deborah A. Martin; Susan L. Wang; Jenny J. Yeh

(57) ABSTRACT

This invention relates to methods for treating obesity by peripheral administration of a trkB antagonist. The invention also relates to compositions and kits comprising a trkB antagonist.

13 Claims, 5 Drawing Sheets

U.S. PATENT DOCUMENTS

Figure 1:
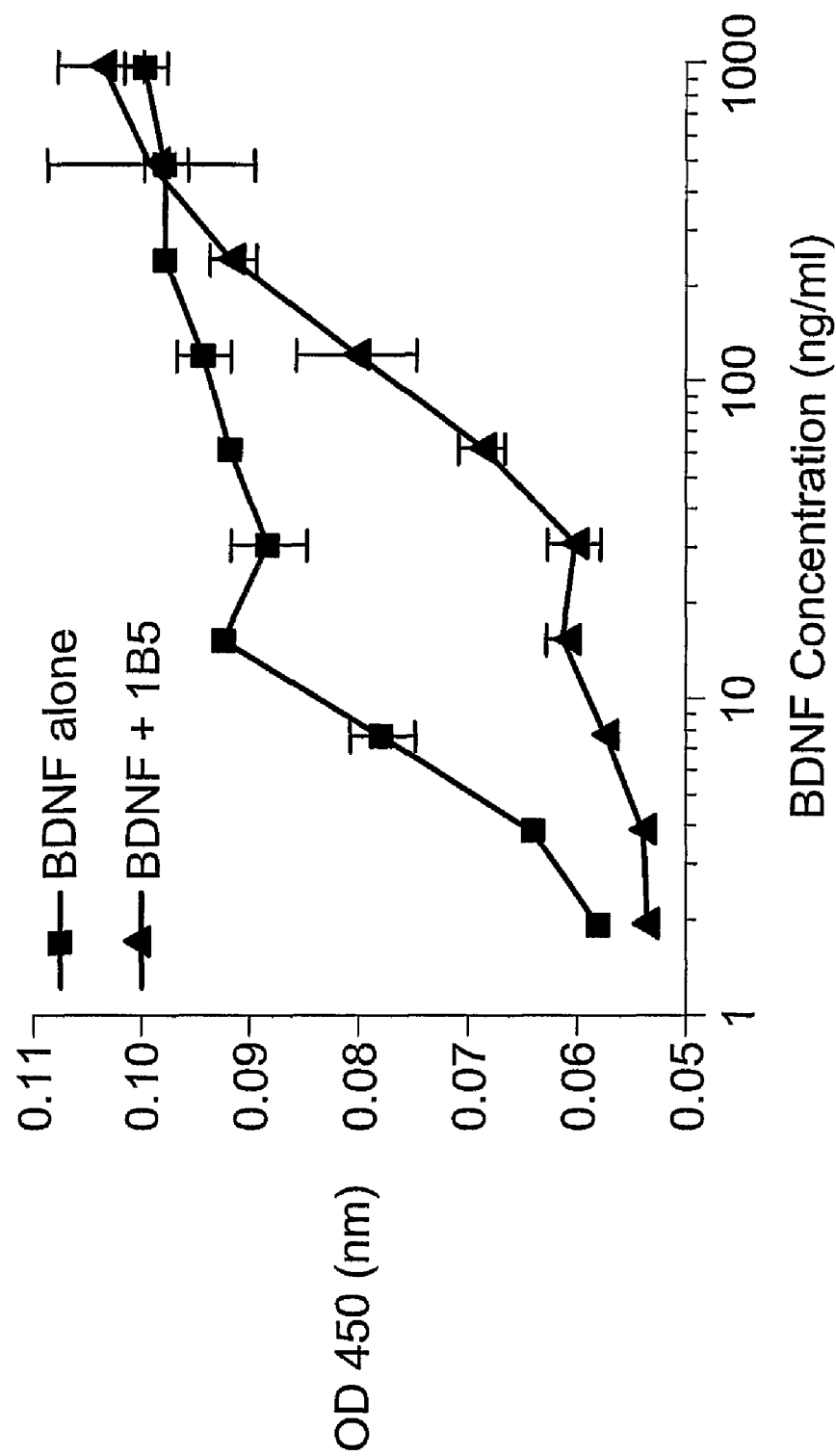

| | | |
|---|---|---|
| 2002/0122829 A1 | 9/2002 | Kishino et al. |
| 2002/0123507 A1 | 9/2002 | Lauffer et al. |
| 2002/0136718 A1 | 9/2002 | Raso |
| 2003/0022840 A1 | 1/2003 | Kishino et al. |
| 2003/0036512 A1 | 2/2003 | Nakagawa et al. |
| 2003/0073655 A1 | 4/2003 | Chain |
| 2003/0105057 A1 | 6/2003 | Fu et al. |
| 2003/0109526 A1 | 6/2003 | Lauffer et al. |
| 2003/0130256 A1 | 7/2003 | Lauffer et al. |
| 2003/0134815 A1 | 7/2003 | Crystal |
| 2003/0144253 A1 | 7/2003 | Mullican et al. |
| 2003/0166537 A1 | 9/2003 | Hanke et al. |
| 2003/0181361 A1 | 9/2003 | Sharma et al. |
| 2003/0186960 A1 | 10/2003 | Lauffer et al. |
| 2003/0191061 A1 | 10/2003 | Brewitt |
| 2003/0191117 A1 | 10/2003 | Lauffer et al. |
| 2003/0203383 A1 | 10/2003 | Rosenthal |
| 2004/0110711 A1 | 6/2004 | Krueger et al. |

FOREIGN PATENT DOCUMENTS

| | | |
|---|---|---|
| EP | 0 298654 A3 | 1/1989 |
| EP | 0 298654 B1 | 1/1989 |
| EP | 0 345 242 A2 | 12/1989 |
| EP | 0 345 242 A3 | 12/1989 |
| EP | 0 524 968 B1 | 2/1993 |
| EP | 1 010 432 A1 | 6/2000 |
| EP | 1 172 113 A1 | 1/2002 |
| EP | 1 231 269 A1 | 8/2002 |
| GB | 2 200 651 A | 8/1988 |
| JP | 10279500 | 10/1998 |
| WO | WO-91/02805 A2 | 3/1991 |
| WO | WO-92/20797 A1 | 11/1992 |
| WO | WO-93/11230 A1 | 6/1993 |
| WO | WO-93/25234 A1 | 12/1993 |
| WO | WO-93/25698 A1 | 12/1993 |
| WO | WO-94/03622 A1 | 2/1994 |
| WO | WO-94/04569 A1 | 3/1994 |
| WO | WO-95/05196 A1 | 2/1995 |
| WO | WO-95/07994 A2 | 3/1995 |
| WO | WO-95/07994 A3 | 3/1995 |
| WO | WO-9511984 A2 | 5/1995 |
| WO | WO-9511984 A3 | 5/1995 |
| WO | WO-96/17072 A2 | 6/1996 |
| WO | WO-96/17072 A3 | 6/1996 |
| WO | WO-97/42338 A1 | 11/1997 |
| WO | WO-99/16460 A2 | 4/1999 |
| WO | WO-99/16460 A3 | 4/1999 |
| WO | WO-00/50089 A2 | 8/2000 |
| WO | WO-00/50089 A3 | 8/2000 |
| WO | WO-00/72871 A1 | 12/2000 |
| WO | WO 01/00662 A2 | 1/2001 |
| WO | WO-01/00662 A3 | 1/2001 |
| WO | WO-01/58891 A2 | 8/2001 |
| WO | WO-01/58891 A3 | 8/2001 |
| WO | WO-03/100016 A2 | 12/2003 |
| WO | WO-03/100016 A3 | 12/2003 |
| WO | WO-2004/110375 A2 | 12/2004 |
| WO | WO 2005/082401 A1 | 9/2005 |
| WO | WO2005082401 | 9/2005 |

OTHER PUBLICATIONS

Aston, R. et al. (May 1989). "Antibody-Mediated Enhancement of Hormone Activity," Mol. Immunol. 26(5):435-446.

Banfield, M.J. et al. (Dec. 2001). "Specificity in Trk Receptor: Neurotrophin Interactions: The Crystal Structure of TrkB-d5 in Complex with Neurotrophin-4/5," Structure 9( 12): 1191-1199.

Barker, P.A. et al. (Mar. 15, 2002). "The MAGE Proteins: Emerging Roles in Cell Cycle ProQression, Apoptosis, and Neurogenetic Disease," J. Neurosci. Res. 67:705-712.

Bonora, E. et al. (Jan. 2000). "Homeostasis Model Assessment Closely Mirrors the Glucose Clamp Technique in the Assessment of Insulin Sensitivity," Diabetes Gare 23:57-63.

Bray, G.A. (Feb. 1992). "Drug Treatment of Obesitv," Am. J. Glin. Nutr. 55(2):538S-544S.

Brommage, R. (2003). "Validation and Calibration of DEXA Body Composition in Mice," Am. J. Physiol Endocrinol. Metab. 285:E454-E459.

Chaldakov, G.N. et al. (Oct. 2003). "Metabotrophic Potential of Neurotrophins: Implication in Obesity and Related Diseases?" Med. Sci. Monit. 9(10):HY19-21.

Chiou, H.C. et al. (1994). "In Vivo Gene Therapy via Receptor-Mediated DNA Delivery," In Gene Therapeutics: Methods and Applications of Direct Gene Transfer JA Wolff, ed. Birkhauser, pp. 143-156.

Connelly, S. et al. (Feb. 1995). "In Vivo Gene Delivery and Expression of Physiological Levels of Functional Human Factor VIII in Mice," Human Gene Therapy 6: 185-193.

Conover, J.C. et al. (May 18, 1995). "Neuronal Deficits, Not Involving Motor Neurons, In Mice Lacking BDNF and/or NT4," Nature 375:235~238.

Courtney, L.P. et al. (1994). "An Anti-IL-2 Antibody Increases Serum Halflife and Improves Anti-Tumor Efficacy of Human Recombinant Interleukin-2," Immunopharmacology 28(3):223-232.

Curiel, D.T. et al. (1992). "High-Efficiency Gene Transfer Mediated by Adenovirus Coupled to DNA-Polylysine Complexes," Human Gene Therapy 3:147-154.

Dayhoff, M.O. et al. (1978). "A Model of Evolutionary Change in Proteins—Matrices for Detecting Distant Relationships" Chapter 22 In Atlas of Protein Sequence and Structure National Biomedical Research Foundation: Washington, DC, 5(Suppl3):345-358.

De Wolf, FA et al. (2000). "Ligand-Binding Proteins: Their Potential for Application in Systems for Controlled Delivery and Uptake of LiQands," Pharm. Rev. 52(2):207-236.

Dicou, E. et al. (1997). "Anti-NGF Autoantibodies and NGF in Sera of Alzheimer Patients and in Normal Subjects in Relation to Age," Autoimmunity 26(3): 189-194.

Dicou, E. et al. (Jan. 1994). "Natural Autoantibodies Against the Nerve Growth Factor in Autoimmune Diseases," J. Neuroimmunol. Erratum 49(1-2):224.

Dicou, E. et al. (May 1997). "Evidence that Natural Autoantibodies Against the Nerve Growth Factor (NGF) May Be Potential Carriers of NGF," J. Neuroimmunol. 75(1-2):200-203.

Dicou, E. et al. (Sep. 1993). "Natural Autoantibodies Against the Nerve Growth Factor in Autoimmune Diseases," *J. Neuroimmunol.* 47(2):159-167.

Duan, W. et al. (Jun. 2003). "Reversal of Behavioral and Metabolic Abnormalities, and Insulin Resistance Syndrome, by Dietary Restriction in Mice Deficient in Brain-Derived Neurotrophic Factor," Endocrinology 144(6):2446-2453.

Duan, W. et al. (Mar. 4, 2003). "Dietary Restriction Normalizes Glucose Metabolism and BDNF Levels, Slows Disease Progression, and Increases Survival in Huntingtin Mutant Mice," Proc. Nat!. Acad. Sci. USA 100(5):2911-2916.

Dyck, P.J. et al. (Feb. 1997). "Intradermal Recombinant Human Nerve Growth Factor Induces Pressure Allodynia and Lowered Heat-Pain Threshold in Humans," Neurology 48(2):501-505.

El-Haschimi, K. et al. (Jun. 2000). "Two Defects Contribute to Hypothalamic Leptin Resistance in Mice with Diet-Induced Obesitv," J. Glin. Invest. 105(12): 1827-1832.

Ernfors, P. et al. (Mar. 10, 1994). "Mice Lacking Brain-Derived Neurotrophic Factor Develop with Sensory Deficits," Nature 368(6467):147-150.

Fan, G. et al. (Apr. 2000). "Knocking the NT4 Gene into the BDNF Locus Rescues BDNF Deficient Mice and Reveals Distinct NT4 and BDNF Activities," Nature Neuroscience 3(4):350-357.

Findeis, M.A. et al. (May 1993). "Targeted Delivery of DNA for Gene Therapy via Receptors," Trends Biotechno/. 11 :202-205.

Ford, E.S. et al. (Jan. 16, 2002). "Prevalence of the Metabolic Syndrome Among US Adults: Findings From the Third National Health and Nutrition Examination Survey," JAMA 287(3):356-359.

Gaertner, H.F. et al. (Jan./Feb. 1996). "Site-Specific Attachment of Functionalized Polv(ethvlene Qlvcol) to the Amino Terminus of Proteins," Bioconjuaate Chern. 7(1 ):38-44.

Gloaguen, I. et al. (Jun. 1997). "Ciliary Neurotrophic Factor Corrects Obesity and Diabetes Associated with Leptin Deficiencv and Resistance," Proc. Nat!. Acad. Sci. USA 94:6456-6461.

Grundy, S.M. et al. (2004). "Definition of Metabolic Syndrome: Report of the National Heart, Lung, and Blood Institute/American Heart Association Conference on Scientific Issues Related to Definition," Circulation 109:433-438.

Hanyu, O. et al. (2003). "Brain-Derived Neurotrophic Factor Modulates Glucagon Secretion from Pancreatic Alpha Cells: Its Contribution to Glucose Metabolism," Diabetes, Obesity and Metabolism 5:27-37.

Hein, J. (1990). "Unified Approach to Alignment and Phylogenes" Chapter 39 in Methods in Enzymoloov Academic Press, Inc.: San Dieoo, CA, 183:626-645.

Higgins, D.G. et al. (Apr. 1989). "Fast and Sensitive Multiple Sequence Alignments on a Microcomputer," CABIOS 5(2):151-153.

Huwyler, J. et al. (Nov. 1996). "Brain Drug Delivery of Small Molecules Using Immunoliposomes," Proc. Nat!. Acad. Sci. USA 93:14164-14169.

International Search Report mailed Jun. 17, 2005 for PCT Application No. PCT/US2005/005881 filed Feb. 22, 2005, five pages.

Jolly, D. (1994). "Viral Vector Systems for Gene Therapy," Cancer Gene Theraoy 1( 1):51-64.

Jones, K.R. et al. (Mar. 25, 1994). "Targeted Disruption of the BDNF Gene Perturbs Brain and Sensory Neuron Development but Not Motor Neuron Development," Cel/76(6):989-999.

Jung, R.T. et al. (Jul. 1991). "Current Therapy: The Management of Obesity," Clinical EndocrinoloaY 35:11-20.

Kang, Y-S. et al. (Apr. 1994). "Use of Neutral Avidin Improves Pharmacokinetics and Brain Delivery of Biotin Bound to an Avidin-Monoclonal Antibody Conjugate," J. Pharmacol. Exp. Ther. 269(1 ):344-350.

Kaplitt, M.G. et al. (Oct. 1994). "Long-Term Gene Expression and Phenotypic Correction Using Adena-Associated Virus Vectors in the Mammalian Brain," Nature Genetics 8:148-153.

Kernie, S.G. et al. (Mar. 15, 2000). "BDNF Regulates Eating Behavior and Locomotor Activity in Mice," EMBO Journal 19(6):1290-1300.

Kimura, O. et al. (1994). "Retroviral Delivery of DNA into the Livers of Transgenic Mice Bearing Premalignant and Malignant Hepatocellular Carcinomas," Human Gene Therapy 5:845-852.

Lee, Y-J. et al. (Apr. 1992). "Successful Weight Loss With Protein-Sparing Modified Fast in a Morbidly Obese Boy with Panhypopituitarism, Diabetes Insipidus, and Defective Thirst Regulation," Clin. Pediatr. 31:234-236.

Leiter, E.H. et al. (Feb. 2004). "Differential Levels of Diabetogenic Stress in Two New Mouse Models of Obesity and Tvpe 2 Diabetes," Diabetes 53(Suppl. 1):S4-S11.

Li, H. et al. (May 2002). "TransferrinlTransferrin Receptor-Mediated Drug Delivery," Med. Res. Rev. 22(3):225-250.

Linnarsson, S. et al. (Dec. 1997). "Learning Deficit in BDNF Mutant Mice," Eur. J. Neurosci. 9(12):2581-2587.

Liu, X. et al. (May 18, 1995). "Sensory but not Motor Neuron Deficits in Mice Lacking NT4 and BDNF," Nature 375:238-241.

Lopez, G.F. et al. (Nov. 8, 2003). "Epithelial Overexpression of BDNF and NTI4 Produce Diverse Gustatory Axon Morphologies," Program No. 38.6, Abstract Viewer/Itinerary Planner, Society for Neuroscience: Washington, DC. Abstract, one page.

Mahato, R.1. et al. (1997). "Cationic Lipid-Based Gene Delivery Systems: Pharmaceutical Perspectives," Pharm. Res. 14(7):853-859.

McMahon, S.B. et al. (Oct. 1995). "Peripheral Neuropathies and Neurotrophic Factors: Animal Models and Clinical Perspectives," Curro Opin. Neurobiol. 5(5):616-624.

Minichiello, L. et al. (Aug. 1998). "Point Mutation in trkB Causes Loss of NT4-Dependent Neurons Without Major Effects on Diverse BDNF Responses," Neuron. 21(2):335-345.

Monteleone et al 2004 also present on the IDS filed Aug. 4, 2008.

Muruganandam, A. et al. (Feb. 2002). "Selection of Phage-Displayed Llama Single-Domain Antibodies that Transmigrate Across Human Blood-Brain Barrier Endothelium," FASEB J. 16:240-242.

Mvers, E.W. et al. (Mar. 1988). "Optimal Alionments in Linear Space," CABIOS 4(1):11-17.

Nakagawa, T. et al. (2003). "Antiobesity and Antidiabetic Effects of Brain-Derived Neurotrophic Factor in Rodent Models of Leptin Resistance," International J. Obesity 27:557-565.

Nakagawa, T. et al. (Mar. 2000). "Brain-Derived Neurotrophic Factor Regulates Glucose Metabolism bv Modulatino Enerov Balance in Diabetic Mice," Diabetes 49:436-444.

Ono, M. et al. (Jan. 2000). "Intermittent Administration of Brain-Derived Neurotrophic Ameliorates Glucose Metabolism in Obese Diabetic Mice," Metabolism 49(1): 129-133.

Ono, M. et al. (Sep. 18, 1997). "Brain-Derived Neurotrophic Factor Reduces Blood Glucose Level in Obese Diabetic Mice but not in Normal Mice," Biochem. Biophys. Res. Commun.238(2):633-637.

Pardridge, W.M. et al. (2000). "Recent Developments in Peptide Drug Delivery to the Brain," Pharmacology & Toxicology 71:3-10.

Philip, R. et al. (Apr. 1994). "Efficient and Sustained Gene Expression in Primary T Lymphocytes and Primary and Cultured Tumor Cells Mediated by Adeno-Associated Virus Plasmid DNA Complexed to Cationic Liposomes," Mol. Cell. Bioi. 14(4):2411-2418.

Qian, Z.M. et al. (Dec. 2002). "Targeted Drug Delivery via the Transferrin Receptor-Mediated Endocvtosis Pathwav," Pharmacol. Rev. 54(4):561-587.

Reifsnyder, P.C. et al. (Mar. 2002). "Deconstructing and Reconstructing Obesity-Induced Diabetes (Diabesity) in Mice," Diabetes' 51:825-832.

Rios, M. et al. (Oct. 2001). "Conditional Deletion of Brain-Derived Neurotrophic Factor in the Postnatal Brain Leads to Obesity and Hyperactivity," Molecular Endocrinology 15(10): 1748-1757.

Roberts, M.J. et al. (2002). "Chemistry for Peptide and Protein PEGylation," Advanced Drug Delivery Reviews 54(2):459-476.

Robinson, D.F. (1971). "Comparison of Labeled Trees with Valency Three," Comb. Theor. 11: 105-119.

Rodriguez-Pena, A. et al. (Nov. 10, 1995). "Expression of Neurotrophins and Their Receptors in Sciatic Nerve of Experimentallv Diabetic Rats," Neurosci. Lett. 200(1):37-40.

Sadick, M.D. et al. (Aug. 1, 1997). "Analysis of NeurotrophinlReceptor Interactions with a gO-Flag-Modified Quantitative Kinase Receptor Activation (gD.KIRA) Enzyme-Linked Immunosorbent Assay," Experimental Cell Research 234(2f:354-361.

Saitou, N. et al. (Jul. 1987). "The Neighbor-Joining Method: A New Method for Reconstructing Phvloaenetic Trees," Mol. Bioi. Evol. 4(4):406-425.

Sakane, T. et al. (1997). "Carboxyl-Directed Pegylation of Brain-Derived Neurotrophic Factor Markedly Reduces Systemic Clearance with Minimal Loss of Biologic Activity," Pharm. Res. 14(8): 1085-1091. . . .

Sevarino, K.A. et al. (Jan. 15, 1988). "Biosynthesis of Thyrotropin-Releasing Hormone by a Rat Medullary Thyroid Carcinoma Cell Line," J. Bioi. Chem. 263(2}:620-623.

Shu, X.-Q. et al. (Apr. 1999). "Effects of trkB and trkC Neurotrophin Receptor Agonists on Thermal Nociception: A Behavioral and Electrophysioloqical StudY," Pain 80(3):463-470.

Sokal, R.R. et al. (1973). "Numerical Taxonomy" In the Principles and Practice of Numerical Taxonomy W.H. Freeman and Company: San Francisco, CA. pp. xi-xvi (Table of Contents Only.).

Steppan, C.M. (Jan. 18, 2001). "The Hormone Resistin Links Obesity to Diabetes," Nature 409:307-312.

Teitelman, G. et al. (Mar. 1998). "Islet Injury Induces Neurotrophin Expression in Pancreatic Cells and Reactive Gliosis of Peri-Islet Schwann Cells," J. Neurobiol. 34(4):304-318.

Tsuchida, A. et al. (2001). "The Effects of Brain-Derived Neurotrophic Factor on Insulin Signal Transduction in the Liver of Diabetic Mice," Diabetologia 44:555-566.

Tsuchida, A. et al. (Sep. 2001). "Acute Effects of Brain-Derived Neurotrophic Factor on Energy Expenditure in Obese Diabetic Mice," Int. J. Obes. Re/at. MetaB. Disord. 25(9):1286-1293.

Wilbur, w'J. et al. (Feb. 1983). "Rapid Similarity Searches of Nucleic Acid and Protein Data Banks," Proc. Natl. Acad. Sci. USA 80:726-730.

Wirth, M.J. et al. (2003). "Accelerated Dendritic Development of Rat Cortical Pyramidal Cells and Interneurons After Biolistic Transfection with BDNF and NT4/5," Development 130(23):5827-5838.

Woffendin, C. et al. (Nov. 1994). "Nonviral and Viral Delivery of a Human Immunodeficiency Virus Protective Gene into Primary Human T Cells," Proc. Natl. Acad. Sci. 91 :11581-11585.

Wu, C.H. et al. (Oct. 15, 1989). "Targeting Genes: Delivery and Persistent Expression of a Foreign Gene Driven by Mammalian Regulatory Elements in Vivo," J. Biol. Chem. 264(29): 16985-16987.

Wu, D. et al. (Jan. 1999). "Neuroprotection with Noninvasive Neurotrophin Delivery to the Brain," *Proc. Natl. Acad. Sci. USA* 96:254-259.

Wu, G.Y. et al. (Apr. 15, 1994). "Incorporation of Adenovirus into a Ligand-Based DNA Carrier System Results in Retention of Original Receptor Specificity and Enhances Targeted Gene Expression," *J. Biol. Chem.* 269(15):11542-11546.

Wu, G.Y. et al. (Aug. 5, 1991). "Receptor-Mediated Gene Delivery in Vivo: Partial Correction of Genetic Analbuminemia in Nagase Rats," *J. Biol. Chem.* 266(22): 14338-14342.

Xu, B. et al. (Jul. 2003). "Brain-Derived Neurotrophic Factor Regulates Energy Balance Downstream of Melanocortin-4 Receptor," *Nature Neuroscience* 6(7):2446-2453.

Yeo, G.S.H. et al. (Nov. 2004). "A de novo Mutation Affecting Human TrkB Associated with Severe Obesity and Developmental Delay," *Nature Neuroscience* 7(11):1187-1189.

Yoshikawa, T. et al. (Nov. 1992). "Biotin Delivery to Brain with a Covalent Conjugate of Avidin and a Monoclonal Antibody to the Transferrin Receptor," *J. Pharmacal. Exp. Ther.* 263(2):897-903.

Zenke, M. et al. (May 1990). "Receptor-Mediated Endocytosis of Transferrin-Polycation Conjugates: An Efficient Way to Introduce DNA into Hematopoietic Cells," *Proc. Natl. Acad. Sci. USA* 87:3655-3659.

Monteleone, Palmiero, et al., "Opposite changes in the serum brain-derived neurotrophic factor in anorexia nervosa and obesity", Phychosomatic Medicine, Sep. 2004, pp. 744-748, vol. 66, No. 5.

International Search Report for International Applicaiton No. PCT/IB2007/000254 dated Jun. 27, 2007.

Pelleymounter, M., et al., "Characteristics of BDNF-Induced Weight Loss," Experimental Neurology, 1995, 229-238, vol. 131.

\* cited by examiner

METHODS FOR TREATING OBESITY BY ADMINISTERING A TRKB ANTAGONIST

This application claims priority, under 35 U.S.C. §119(e), from U.S. provisional application Ser. No. 60/764,864, filed Feb. 2, 2006, incorporated herein by reference.

FIELD OF THE INVENTION

This invention concerns use of trkB antagonists in the treatment and/or prevention of obesity.

BACKGROUND OF THE INVENTION

Obesity is a chronic disease and a major health concern in modern society. About 30% adults in U.S. are obese, and about 65% adults are overweight. Obesity is associated not only with a social stigma, but also with decreased life span and numerous health problems, including hypertension; type 2 diabetes mellitus; elevated plasma insulin concentrations; insulin resistance; dyslipidemia; hyperlipidemia; endometrial, breast, prostate and colon cancer; osteoarthritis; respiratory complications, such as obstructive sleep apnea; cholelithiasis; gallstones; arteriosclerosis; heart disease; abnormal heart rhythms; and heart arrhythmias. Kopelman, P. G., Nature 404, 635-643 (2000).

Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. Jung and Chong, Clinical Endocrinology, 35: 11-20 (1991); Bray, Am. J. Clin. Nutr., 55: 538S-544S (1992). Protein-sparing modified fasting has been reported to be effective in weight reduction in adolescents. Lee et al., Clin. Pediatr., 31: 234-236 (April 1992). However, existing therapies are not very effective for a lot of obese patients. For the most severe obese patients, surgical intervention may be required. Considering the high prevalence of obesity in our society and the serious consequences associated therewith as discussed above, any therapeutic drug potentially useful in reducing weight of obese persons could have a profound beneficial effect on their health. There is a need for a drug that reduces total body weight of obese subjects toward their ideal body weight without significant adverse side effects and that helps the obese subject maintain the reduced weight level.

Neurotrophins are a family of small, homodimeric proteins, which play a crucial role in the development and maintenance of the nervous system. Members of the neurotrophin family include nerve growth factor (NGF), brain-derived neurotrophic factor (BDNF), neurotrophin-3 (NT-3), neurotrophin-4/5 (NT-4/5), neurotrophin-6 (NT-6), and neurotrophin-7 (NT-7). Neurotrophins, similar to other polypeptide growth factors, affect their target cells through interactions with cell surface receptors. According to current knowledge, two kinds of transmembrane glycoprotein's serve as receptors for neurotrophins. Neurotrophin-responsive neurons possess a common low molecular weight (65-80 kDa), low affinity receptor (LNGFR), also known as p75NTR or p75, which binds NGF, BDNF, NT-3 and NT-4/5 with a $K_D$ of $2\times10^{-9}$ M; and large molecular weight (130-150 kDa), high-affinity ($K_D$ in the $10^{-11}$ M range) receptors, which are members of the trk family of receptor tyrosine kinases. The identified members of the trk receptor family are trkA, trkB, and trkC.

Both BDNF and NT-4/5 bind to the trkB and p75NTR receptors with similar affinity. However, NT-4/5 and BDNF mutant mice exhibit quite contrasting phenotypes. Whereas NT-4/5$^{-/-}$ mice are viable and fertile with only a mild sensory deficit, BDNF$^{-/-}$ mice die during early postnatal stages with severe neuronal deficits and behavioral symptoms. Fan et al., Nat. Neurosci. 3(4):350-7, 2000; Liu et al., Nature 375:238-241, 1995; Conover et al., Nature 375:235-238, 1995; Ernfors et al., Nature 368:147-150, 1994; Jones et al., Cell 76:989-999, 1994. Several publications report that NT-4/5 and BDNF have distinct biological activities in vivo and suggest that the distinct activities may result partly from differential activation of the trkB receptor and its down-stream signaling pathways by NT-4/5 and BDNF. Fan et al., Nat. Neurosci. 3(4): 350-7, 2000; Minichiello et al., Neuron. 21:335-45, 1998; Wirth et al., Development. 130(23):5827-38, 2003; Lopez et al., Program No. 38.6, 2003 Abstract, Society for Neuroscience.

It has been shown that BDNF and NT-4/5 have blood glucose and blood lipid controlling activity and anti-obesity activity in type II diabetic model animals, such as C57db/db mice. U.S. Pat. No. 6,391,312; Itakura et al., Metabolism 49:129-33 (2000); U.S. App. Pub. No. 2005/0209148; PCT WO 2005/082401. It has also been shown that BDNF has anti-obesity activity and activity of ameliorating leptin resistance in mice fed with high fat diet. U.S. Pub. No. 2003/0036512. Kernie et al. reported that BDNF or NT-4/5 could transiently reverse the eating behavior and obesity in heterozygous BDNF knock out mice in which BDNF gene expression was reduced. Kernie et al., EMBO J. 19(6):1290-300, 2000. It has been reported that a de novo missense mutation of Y722C substitution on human trkB results in impaired receptor phosphorylation and signaling to MAP kinase; and this mutation seems to result in a unique human syndrome of hyperphagic obesity. Yeo et al., Nat. Neurosci. 7:1187-1189 (2004).

Circulating levels of BDNF in people with obesity and in patients with anorexia nervosa have been studied. Monteleone et al., Psychosomatic Medicine 66:744-748, 2004; Nakazato et al., Biol. Psychiatry 54:485-490, 2003. Contrary to the prediction based on the findings that impairments of BDNF production in mice have been associated with increased food intake, reduced energy expenditure, and weight gain, circulating BDNF is significantly reduced in the anorexia nervosa patients and significantly increased in obese subjects as compared with the non-obese healthy controls. It has been hypothesized that in anorexia nervosa, BDNF reduction, by promoting food intake, attempts to counterbalance the patients' altered behaviors that lead to a negative balance; and in obesity, increased levels of BDNF may represent an adaptive mechanism to counteract the condition of positive energy imbalance by stimulating energy expenditure and decreasing food ingestion. Monteleone et al., Psychosomatic Medicine 66:744-748, 2004.

All patents, patent applications, and publications cited herein are hereby incorporated by reference in their entirety.

BRIEF SUMMARY OF THE INVENTION

The present invention provides methods for decreasing body weight and/or food intake by peripheral administration of a trkB antagonist. These methods can be used for treating or preventing obesity or hyperphagic (over-eating) disorders (e.g., bulimia and Prader-Willi syndrome).

In one aspect, the invention provides methods for controlling (including decreasing) body weight in an individual comprising peripherally administering to the individual an effective amount of a trkB antagonist.

In another aspect, the invention provides methods for controlling (including decreasing) food intake in an individual comprising peripherally administering to the individual an effective amount of a trkB antagonist.

In some embodiments, the individual is obese. In some embodiments, the individual is at risk of obesity or is overweight. In some embodiments, the individual is suffering from overeating and obesity in the context of a congenital disease such as Prader-Willi syndrome. In some embodiments, the individual is suffering from binge-eating without obesity in the context of an eating disorder such as bulimia nervosa.

In another aspect, the invention provides methods for treating obesity (including managing obesity) in an individual comprising peripherally administering to the individual an effective amount of a trkB antagonist. Treatment of obesity includes treating an individual whose body weight has been reduced after treatment and is no longer obese.

In another aspect, the invention provides methods for delaying the development or progression of obesity in an individual comprising peripherally administering to the individual an effective amount of a trkB antagonist. In some embodiments, the onset of the obesity is delayed. In other embodiments, the progression of the obesity (for example, development of obesity associated complications, increase of BMI) is delayed. In some embodiments, development of obesity in the individual is prevented. In some embodiments, the development of complications associated with obesity in the individual is prevented. In some embodiments, the individual is at risk of obesity or is overweight.

In some embodiments, the individual is a human.

The present invention provides for a method for treating obesity or a condition of being overweight in a mammal in need of such treatment, comprising peripherally administering to the mammal a therapeutically effective amount of a trkB antagonist or a pharmaceutically acceptable salt thereof. In preferred embodiments, the trkB antagonist is an anti-BDNF antibody, an anti-trkB antagonist antibody, a trkB-Fc fusion protein, and the mammal is a human.

The invention also provides a method of inhibiting weight gain, reducing food intake or reducing caloric intake in a mammal in need of such treatment, comprising peripherally administering to the mammal a therapeutically effective amount of a trkB antagonist or a pharmaceutically acceptable salt thereof. In preferred embodiments, the trkB antagonist is an anti-BDNF antibody, the trkB antagonist is an anti-trkB antagonist antibody, the trkB antagonist is trkB-Fc fusion protein, and the mammal is a human.

The invention also provides for the above described methods in which the trkB antagonist or pharmaceutically acceptable salt thereof is administered in combination with a second agent that is an anti-obesity agent.

The invention also provides for the use of a trkB antagonist in the manufacture of a medicament for treating obesity or a condition of being overweight in a mammal or for inhibiting weight gain, reducing food intake or reducing caloric intake in a mammal. In preferred embodiments, the trkB antagonist is an anti-BDNF antibody, a trkB antagonist antibody, or a trkB-Fc fusion protein, and the mammal is a human.

The trkB antagonist is administered peripherally. For example, the trkB antagonist may be administered by one of the following means: intravenously, intraperitoneally, intramuscularly, subcutaneously, parenterally, via inhalation, intraarterially, intracardially, intraventricularly, and transdermally.

An exemplary trkB antagonist that can be used for the methods described herein includes, but is not limited to, an anti-BDNF antibody, an anti-NT-4/5 antibody, an anti-trkB antibody, and a trkB immunoadhesin.

In another aspect, the invention provides pharmaceutical compositions comprising an effective amount of a trkB antagonist and a pharmaceutically acceptable excipient. The pharmaceutical compositions may be used for treating or preventing any of the diseases described herein.

In another aspect, the invention provides kits comprising a trkB antagonist for use in any of the methods described herein. In some embodiments, the kits comprise a container, a composition comprising an effective amount of a trkB antagonist, in combination with a pharmaceutically acceptable excipient, and instructions for using the composition in any of the methods described herein.

BRIEF DESCRIPTION OF THE DRAWING(S)

FIG. 1 is a graph showing the trkB tyrosine phosphorylation dose response to BDNF in the presence or the absence of 1B5 anti-BDNF antibody. The X-axis represents the different concentration of BDNF added to the culture of trkB-expressing Chinese hamster ovary (CHO) cells. The Y-axis represents the level of trkB tyrosine phosphorylation as detected by ELISA. The data indicated that the trkB tyrosine phosphorylation induced by BDNF was significantly reduced by the presence of 1B5 antibody supernatant.

Figure 2A:
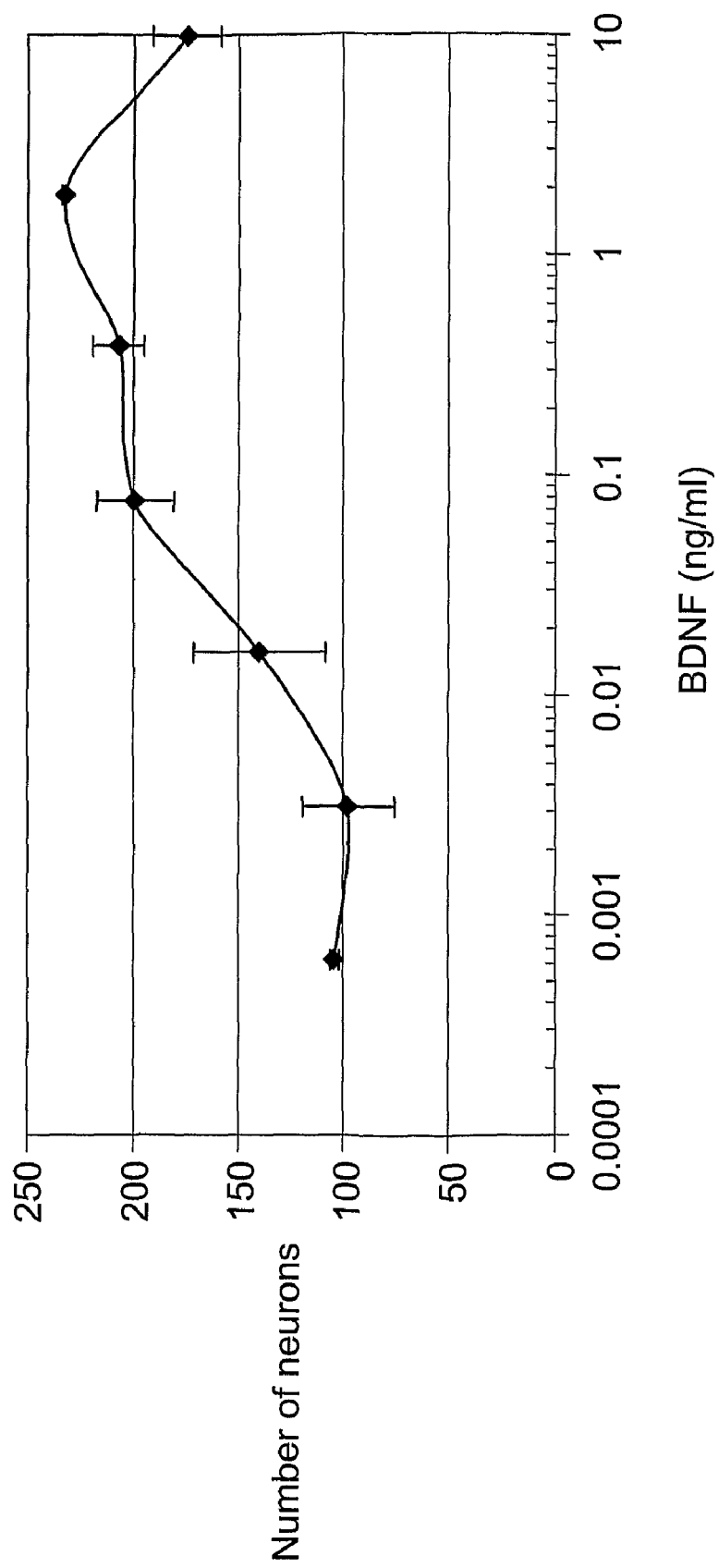

FIG. 2A is a graph of the nodose neuron survival dose response to BDNF alone. The X-axis represents the different concentration of BDNF added to the embryonic day 18 (E18) nodose neuron culture obtained from CD-1 mice. The Y-axis represents the number of surviving neurons 48 hours post plating. The data indicated that maximal neuron survival was achieved with BDNF from 0.1-0.5 ng/ml.

Figure 2B:
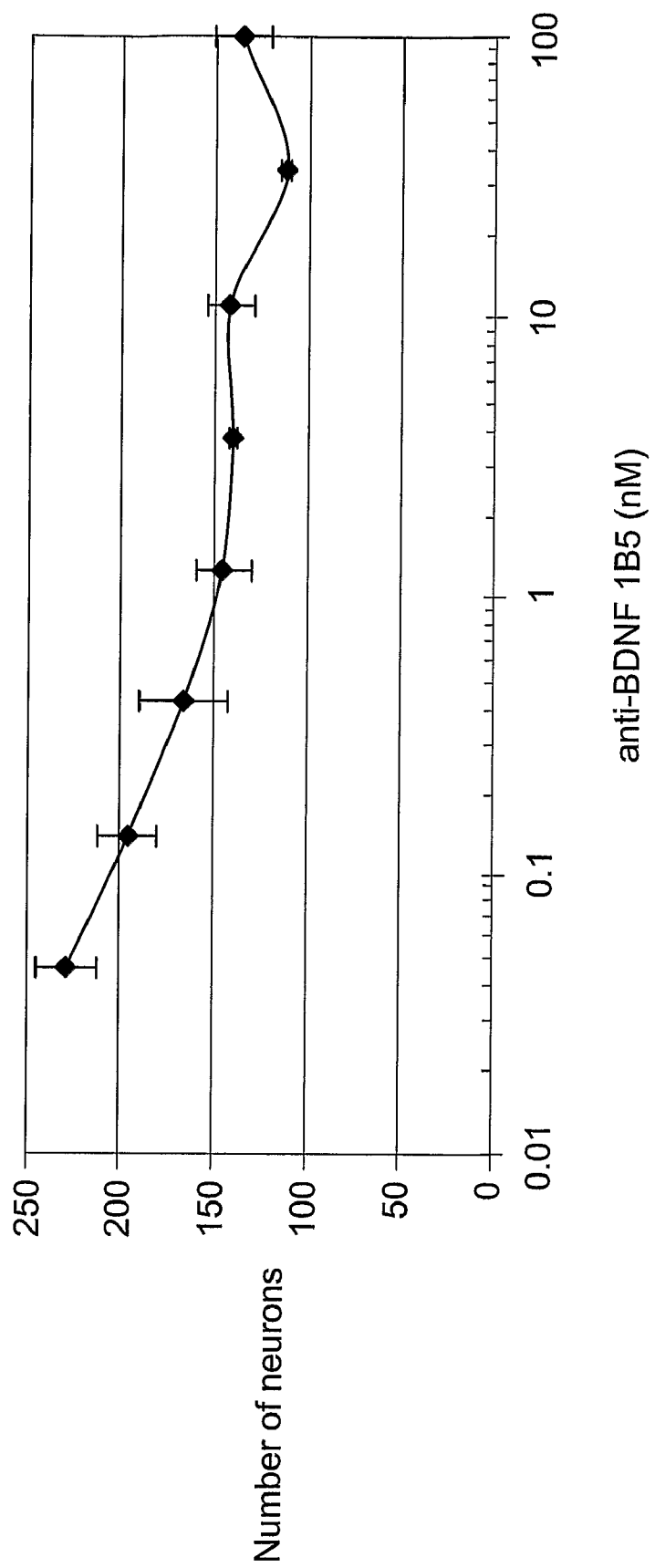
Figure 3A:
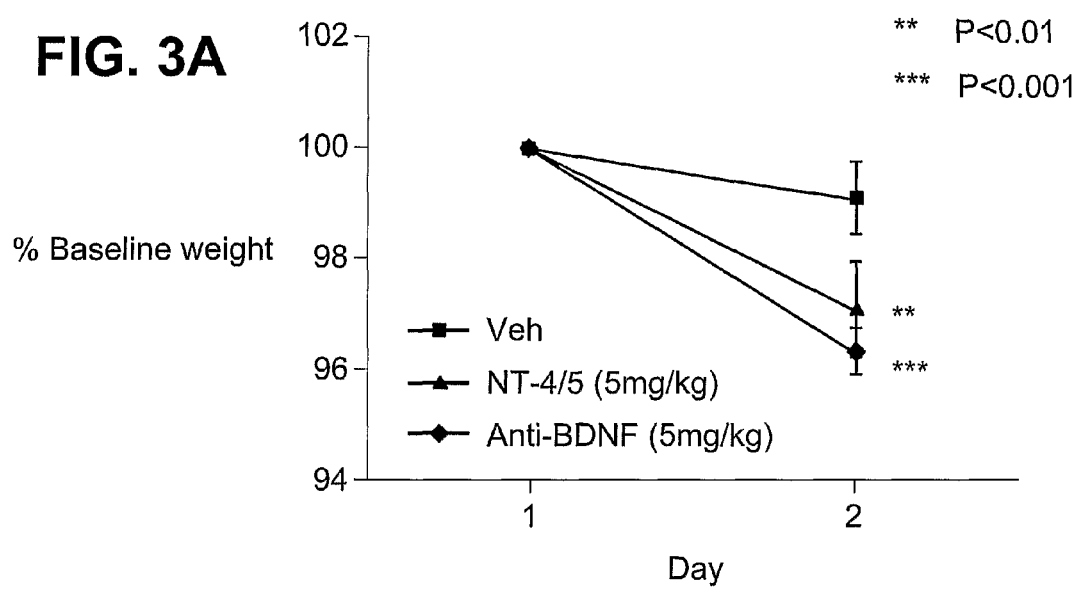
Figure 3B:
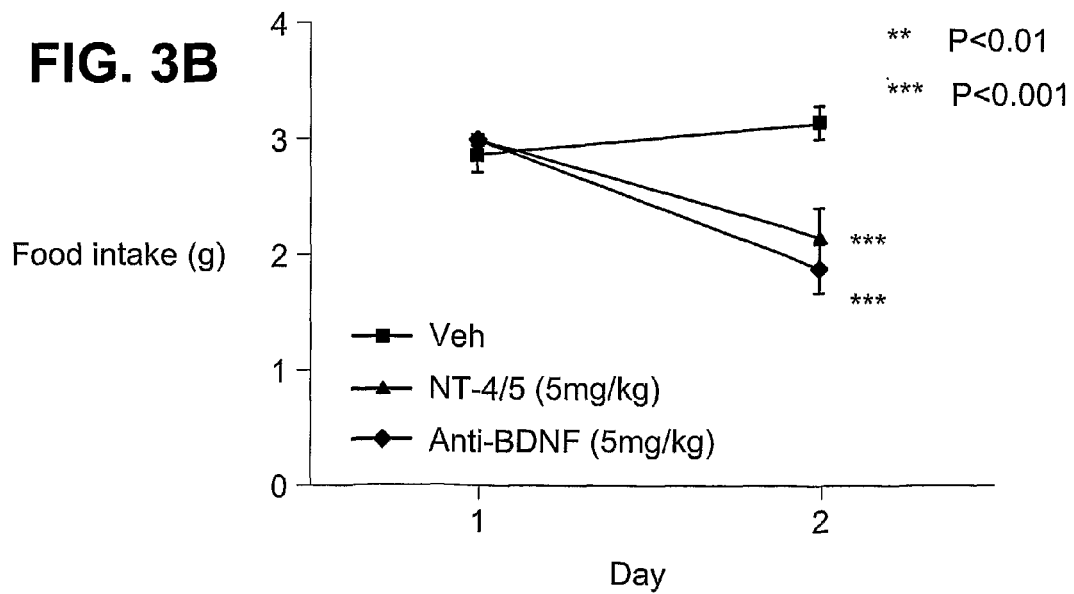

FIG. 2B is a graph of the nodose neuron survival in the presence of saturating concentration (0.5 ng/mL) of BDNF and increasing concentrations of 1B5 anti-BDNF antibody. The X-axis represents the different concentrations of 1B5 anti-BDNF antibody added to the embryonic day 18 (E18) nodose neuron culture obtained from CD-1 mice. The Y-axis represents the number of surviving neurons 48 hours post plating. The data indicated that the 50% effective blocking concentration (EC50) of 1B5 antibody under this condition was about 0.4-1 nM FIG. 3A and FIG. 3B are graphs showing the effect of peripheral injection of anti-BDNF antibody (clone 1B5) on body weight (FIG. 3A) and food intake (FIG. 3B) in high fat diet induced obese (DIO) mice. In FIG. 3A, the X axis corresponds to days when body weight was measured and the Y axis corresponds to body weight measured as a percentage of the baseline (body weight before any treatment). Data indicated that body weight of both anti-BDNF antibody treated group and NT-4/5 treated group was significantly different from the vehicle group one day after the injection (Two way ANOVA with Bonderroni post-tests, P<0.001 for anti-BDNF antibody treated group as compared to the vehicle group; and P<0.01 for NT-4/5 treated group as compared to the vehicle group). In FIG. 1B, the X axis corresponds to days when food intake was measured and the Y axis corresponds to food taken by a mouse per day. Data indicated that food intake of both anti-BDNF antibody treated group and NT-4/5 treated group was significantly different from the vehicle group (P<0.001 for anti-BDNF antibody treated group as compared to the vehicle group; and P<0.001 for NT-4/5 treated group as compared to the vehicle group).

Figure 4A:
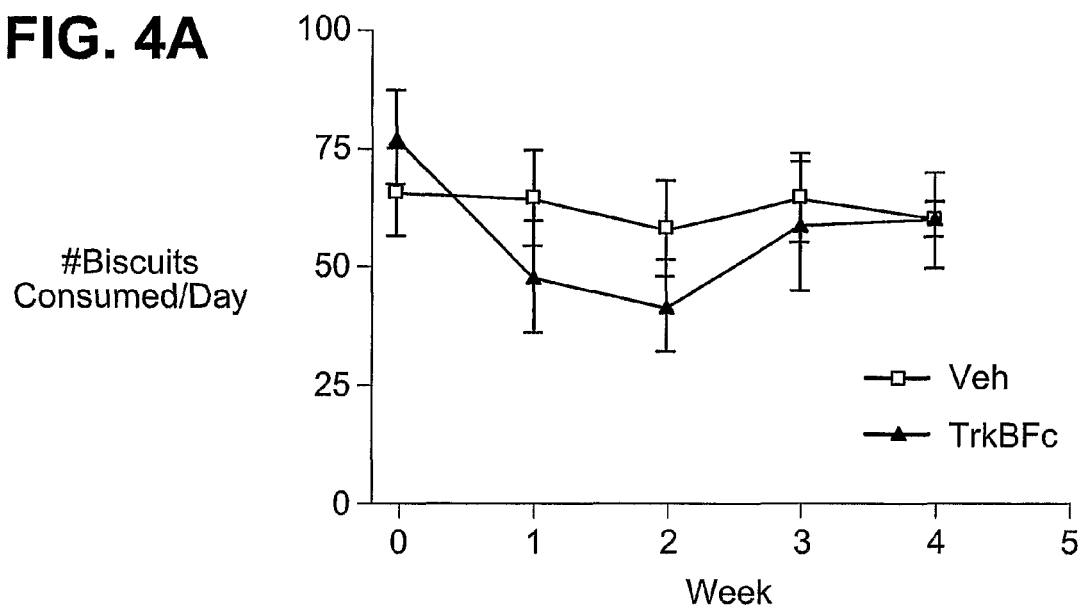
Figure 4B:
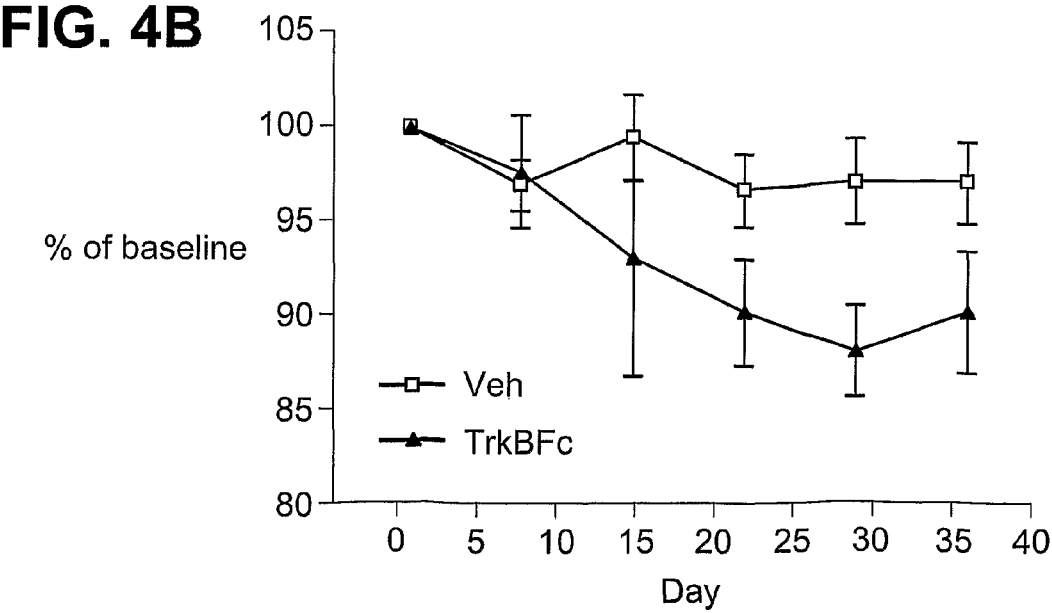

FIG. 4A and FIG. 4B are graphs showing the effect of peripheral injection of recombinant human trkB-Fc fusion protein on average daily food intake and body mass index (BMI), respectively. After 30 days of treatment, there was a trend towards decreased food intake and a significant decrease in BMI (P=0.0083, F=8.285, 2-way ANOVA).

DETAILED DESCRIPTION OF THE INVENTION

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook, at al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel, at al., eds., 1987); *PCR: The Polymerase Chain Reaction*, (Mullis, at al., eds., 1994); *Current Protocols in Immunology* (J. E. Coligan at al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

II. Definitions

As used herein, "obesity" is a condition in which there is an excess of body fat in a subject. Obesity may be due to any cause, whether genetic or environmental. The operational definition of obesity is based on the Body Mass Index (BMI), which is calculated as body weight per height in meters squared ($kg/m^2$). Generally, "Obesity" refers to a condition whereby an otherwise healthy subject has a Body Mass Index (BMI) greater than or equal to 30.0 $kg/m^2$, or a condition whereby a subject with at least one co-morbidity has a BMI greater than or equal to 27.0 $kg/m^2$. An "obese subject" is an otherwise healthy subject with a Body Mass Index (BMI) greater than or equal to 30.0 $kg/m^2$ or a subject with at least one co-morbidity with a BMI greater than or equal to 27.0 $kg/m^2$. An obese subject may have a BMI of at least about any of 31.0, 32.0, 33.0, 34.0, 35.0, 36.0, 37.0, 38.0, 39.0, and 40.0. A "overweight subject" is a subject with a BMI of 25.0 to 29.9 $kg/m^2$.

Different countries may define obesity and overweight with different BMI. The term "obesity" is meant to encompass definitions in all countries. For example, the increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25.0 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25.0 $kg/m^2$.

Obesity-induced or obesity-related co-morbidities include, but are not limited to, diabetes, non-insulin dependent diabetes mellitus-type II, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

An individual "at risk" of obesity may or may not have detectable disease, and may or may not have displayed detectable disease prior to the treatment methods described herein. "At risk" denotes that an individual has one or more so-called risk factors, which are measurable parameters that correlate with development of obesity. An individual having one or more of these risk factors has a higher probability of being obese than an individual without these risk factor(s). These risk factors include, but are not limited to, age, diet, physical inactivity, metabolic syndrome, family history of obesity, ethnicity, hereditary syndromes, history of previous disease (e.g. eating disorder, metabolic syndrome, and obesity), presence of precursor disease (e.g., overweight). For example, an otherwise healthy individual with a BMI of 25.0 to less than 30.0 $kg/m^2$ or an individual with at least one co-morbidity with a BMI of 25.0 $kg/m^2$ to less than 27.0 $kg/m^2$ is at risk of obesity.

As used herein, "treatment" is an approach for obtaining beneficial or desired clinical results. For purposes of this invention, beneficial or desired clinical results include, but are not limited to, one or more of the following: improving, lessening severity, alleviation of one or more symptoms associated with a disease. For obesity, beneficial or desired clinical results include any one or more of the following: reducing or maintaining body weight; controlling (including reducing) food intake or calorie intake; increasing metabolic rate or inhibiting reduction of metabolic rate; and improving, lessening severity, and/or alleviating any of the disorders associated with obesity, such as diabetes, non-insulin dependent diabetes mellitus, hyperglycemia, low glucose tolerance, insulin resistance, lipid disorder, dyslipidemia, hyperlipidemia, hypertriglyceridemia, hypercholesterolemia, abdominal obesity, eating disorder, metabolic syndrome, hypertension, osteoarthritis, myocardial infarction, stroke and other associated diseases; increasing the quality of life of those suffering from the obesity, and/or prolonging lifespan.

As used herein, "delaying" development of obesity means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. For example, one outcome of delaying development may be reducing the body weight of a subject at risk of obesity relative to that subject's body weight immediately before the administration of the compositions described herein. Another outcome of delaying development may be preventing regain of body weight previously lost as a result of diet, exercise, or pharmacotherapy. Another outcome of delaying development may be preventing obesity from occurring if the treatment is administered prior to the onset of obesity in a subject at risk of obesity. Another outcome of delaying development may be decreasing the occurrence and/or severity of obesity-related disorders if the treatment is administered prior to the onset of obesity in a subject at risk of obesity.

"Development" of obesity means the onset and/or progression of the disease within an individual (which can be different embodiments of the invention). Obesity development can be detectable using standard clinical techniques as described herein. However, development also refers to disease progression that may be initially undetectable. For purposes of this invention, progression refers to the biological course of the disease state, in this case, as determined by assessing height and weight for estimating BMI, measuring waist circumference, assessing co-morbidities, as well as the onset and/or worsening of obesity complications such as arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis. A variety of these diagnostic tests are known in the art. "Development" includes occurrence, recurrence, and onset. As used herein "onset" or "occurrence" of obesity includes initial onset and and/or recurrence.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing intensity, duration, or frequency of attack of the disease, and decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. For example, an effective amount of a trkB antagonist for treating obesity is an amount sufficient to treat or ameliorate one or more symptoms associated with obesity. An "effective amount" is an amount sufficient to result in one or more of the following (which can also correspond to various embodiments of the invention): reducing or controlling body weight, controlling food intake, increasing metabolic rate, decreasing one or more symptoms resulting from the diseases associated with obesity, increasing the quality of life of those suffering from the obesity, and/or prolonging lifespan.

As used herein, "controlling body weight" or "improvement in body weight" refers to reducing or maintaining the body weight in an individual (as compared to the level before treatment). In some embodiments, the body weight is generally maintained within the normal range. The body weight may be reduced by reducing the calorie intake and/or reducing the body fat accumulation. In some embodiments, the body weight is reduced at least about any of 5%, 10%, 20%, 30%, 40%, or 50% in the individual as compared to the level before treatment.

As used herein, "controlling food intake" refers to reducing or maintaining the food intake in an individual (as compared to the level before treatment). In some embodiments, the food intake is generally maintained in the normal range. In some embodiments, the food intake is reduced by about any of 5%, 10%, 20%, 30%, 40%, 50%, or 60% in the individual as compared to the level before treatment.

An "individual" or a "subject" is a mammal, more preferably, a human. Mammals also include, but are not limited to, farm animals, sport animals, pets, primates (including humans), horses, dogs, cats, mice and rats.

A "trkB antagonist" refers to an agent that is able to block, suppress or reduce (including significantly) trkB biological activity, including downstream pathways mediated by trkB signaling, such as binding of trkB to BDNF or NT-4/5 and/or elicitation of a cellular response to BDNF or NT-4/5. The term "antagonist" implies no specific mechanism of biological action whatsoever, and is deemed to expressly include and encompass all possible pharmacological, physiological, and biochemical interactions with trkB whether direct or indirect, or whether interacting with BDNF, NT-4/5, trkB, or through another mechanism, and its consequences which can be achieved by a variety of different, and chemically divergent, compositions. Exemplary trkB antagonists include, but are not limited to, an anti-BDNF antibody, an anti-NT-4/5 antibody, a BDNF or an NT-4/5 inhibitory compound, a BDNF or an NT-4/5 structural analog, a dominant-negative mutation of a trkB receptor that binds BDNF and/or NT-4/5, a trkB immunoadhesin, an anti-trkB antibody, and a trkB inhibitory compound. For purpose of the present invention, it will be explicitly understood that the term "antagonist" encompass all the previously identified terms, titles, and functional states and characteristics whereby the trkB receptor itself, a trkB biological activity (including but not limited to its ability to mediate any aspect of body weight and food intake), or the consequences of the biological activity, are substantially nullified, decreased, or neutralized in any meaningful degree.

"Biological activity" of trkB receptor generally refers to the ability to bind BDNF and NT-4/5 and/or activate trkB receptor signaling pathways. Without limitation, a biological activity includes any one or more of the following: the ability to bind its ligand BDNF and/or NT-4/5; the ability to dimerize and/or autophosphorylate after the ligand binding; the ability to activate the trkB signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage; and the ability to mediate body weight and/or food intake.

An "anti-BDNF antibody" (interchangeably termed "anti-BDNF antagonist antibody") refers to an antibody that is able to bind to BDNF and inhibit activation of trkB by BDNF and/or downstream pathway(s) mediated by the trkB signaling function.

An "anti-NT-4/5 antibody" (interchangeably termed "anti-NT-4/5 antagonist antibody") refers to an antibody that is able to bind to NT-4/5 and inhibit activation of trkB by NT-4/5 and/or downstream pathway(s) mediated by the trkB signaling function.

An "anti-trkB antibody" (interchangeably termed "anti-trkB antagonist antibody") refers to an antibody that is able to bind to trkB and inhibit activation of trkB by BDNF and/or NT-4/5 and/or downstream pathway(s) mediated by the trkB signaling function.

A "trkB immunoadhesin" refers to a soluble chimeric molecule comprising a fragment of a trkB receptor, for example, the extracellular domain of a trkB receptor and an immunoglobulin sequence, which retains the binding specificity of the trkB receptor.

As used herein, "peripheral administration" or "administered peripherally" refers to introducing an agent into a subject outside of the central nervous system or blood brain barrier. Peripheral administration encompasses any route of administration other than direct administration to the spine or brain. Peripheral administration can be local or systemic.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refer to forms of non-human (e.g., murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, and six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a trkB epitope is an antibody that binds this epitope with greater affinity, avidity, more readily, and/or with greater duration than it binds to other trkB epitopes or non-trkB epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; de Haas et al., 1995, J. Lab. Clin. Med., 126:330-41; Nimmerjahn et al., 2005, Immunity 23:2-4. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably, at least about 95%, at least about 96%, at least about 97%, at least about 98%, at least about 99% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or U.S. Pat. No. 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000).

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, □-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "substantially pure" refers to material which is at least 50% pure (i.e., free from contaminants), more preferably, at least 90% pure, more preferably, at least 95% pure, more preferably, at least 98% pure, more preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

As used herein, the singular form "a", "an", and "the" includes plural references unless indicated otherwise.

III. Methods of the Invention

The present invention encompasses methods for controlling body weight and/or food intake by peripheral administration of a trkB antagonist. These methods can be used for treating or preventing obesity or hyperphagic (over-eating) disorders in mammals. The methods entail peripheral administration of an effective amount of one or more trkB antagonists to an individual in need thereof (various indications and aspects are described herein).

With respect to all methods described herein, reference to trkB antagonists also include compositions comprising one or more of these agents. These compositions may further comprise suitable excipients, such as pharmaceutically acceptable excipients including buffers, which are well known in the art. The present invention can be used alone or in combination with other conventional methods of treatment.

The trkB antagonist is administered peripherally. It is understood that although the agent is administered peripherally, a small percentage of the agent may pass blood brain barrier and result in delivery to the central nervous system depending on the properties of the agent. In some embodiments, less than any of about 1%, about 0.5%, about 0.25%, and about 0.1% of peripherally administered trkB antagonist (for example, trkB antagonist antibody) gains access to the CNS.

The trkB antagonist can be administered to an individual via any suitable peripheral route. It should be apparent to a person skilled in the art that the examples described herein are not intended to be limiting but to be illustrative of the techniques available. Accordingly, in some embodiments, the trkB antagonist is administered to an individual in accord with known methods, such as intravenous administration, e.g., as a bolus or by continuous infusion over a period of time, by intramuscular, intraperitoneal, subcutaneous, intraarticular, sublingually, intrasynovial, via insufflation, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, trkB antagonist can be aerosolized using a fluorocarbon formulation and a metered dose inhaler, or inhaled as a lyophilized and milled powder.

A trkB antagonist may be administered via site-specific or targeted local delivery techniques outside of the CNS. Examples of site-specific or targeted local delivery techniques include various implantable depot sources of the trkB antagonist or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of trkB antagonists may be used for administration. In some embodiments, a trkB antagonist may be administered neat. In other embodiments, a trkB antagonist and a pharmaceutically acceptable excipient are administered, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000). Generally, these agents are formulated for administration by injection (e.g., intraperitoneally, intravenously, subcutaneously, intramuscularly, etc.), although other forms of administration (e.g., oral, mucosal, transdermal, inhalation, etc) can be also used.

The particular dosage regimen, i.e., dose, timing and repetition, will depend on the particular individual and that individual's medical history, the particular and the stage of the disease (e.g., obesity) to be treated, and the particular trkB antagonist. Generally, any of the following doses of trkB antagonist (e.g., anti-BDNF, anti-NT-4/5, and anti-trkB antagonist antibody) may be used: a dose of at least about 50 mg/kg body weight; at least about 20 mg/kg body weight; at least about 10 mg/kg body weight; at least about 5 mg/kg body weight; at least about 3 mg/kg body weight; at least about 2 mg/kg body weight; at least about 1 mg/kg body weight; at least about 750 µg/kg body weight; at least about 500 µg/kg body weight; at least about 250 ug/kg body weight; at least about 100 µg/kg body weight; at least about 50 µg/kg body weight; at least about 10 ug/kg body weight; at least about 1 µg/kg body weight, or more, is administered. Empirical considerations, such as the half-life, generally will contribute to determination of the dosage. For repeated administrations over several days or longer, depending on the condition, the treatment is sustained until a desired suppression of disease symptoms occurs or until sufficient therapeutic levels are achieved. For example, dosing from one to five times a week is contemplated. Other dosing regimens include a regimen of up to 1 time per day, 1 to 5 times per week, or less frequently. In some embodiments, the trkB antagonist is administered about once per week, about 1 to 4 times per month. Intermittent dosing regime with staggered dosages spaced by 2 days up to 7 days or even 14 days may be used. In some embodiments, treatment may start with a daily dosing and later change to weekly even monthly dosing. The progress of this therapy is easily monitored by conventional techniques and assays.

In some individuals, more than one dose may be required. Frequency of administration may be determined and adjusted over the course of therapy. For example, frequency of administration may be determined or adjusted based on the type and severity of the disease to be treated, whether the agent is administered for preventive or therapeutic purposes, previous therapy, the patient's clinical history and response to the agent, and the discretion of the attending physician. Typically the clinician will administer a trkB antagonist until a dosage is reached that achieves the desired result. In some cases, sustained continuous release formulations of trkB antagonist may be appropriate. Various formulations and devices for achieving sustained release are known in the art. For example, trkB antagonist may be administered through a mechanical pump or embedded in a matrix bed for sustained or slow release.

In one embodiment, dosages for a trkB antagonist may be determined empirically in individuals who have been given one or more administration(s). Individuals are given incremental dosages of a trkB antagonist. To assess efficacy of a trkB antagonist, markers of the disease state can be monitored. It will be apparent to one of skill in the art that the dosage will vary depending on the individual, the stage of the disease (e.g., stage of obesity), and the past and concurrent treatments being used.

Administration of a trkB antagonist in accordance with the method in the present invention can be continuous or intermittent, depending, for example, upon the recipient's physiological condition, whether the purpose of the administration is therapeutic or prophylactic, and other factors known to skilled practitioners. The administration of a trkB antagonist may be essentially continuous over a preselected period of time or may be in a series of spaced doses.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

Assessment of disease is performed using standard methods known in the arts, for example, by monitoring appropriate marker(s). For example, the following markers may be monitored for obesity: body weight, Body Mass Index (BMI), body composition study, food or calorie intake, behavioral measurement of hunger and satiety, metabolic rate, and obesity-related co-morbidities (such as hyperlipidemia and hypertension).

IV. Compositions and Methods of Making the Compositions

The methods of the invention use a trkB antagonist, which refers to any molecule that suppresses or reduces (including significantly) trkB biological activity, including downstream pathways mediated by trkB signaling, such as binding of trkB to its ligand BDNF or NT-4/5, and/or elicitation of a cellular response to BDNF or NT-4/5. Exemplary trkB antagonists include, but are not limited to, an anti-BDNF antibody, an anti-NT-4/5 antibody, an antibody that binds and inhibits the BDNF-NT-4/5 heterodimer, a BDNF or an NT-4/5 inhibitory compound (for example, a compound that interferes with or compromises trkB-ligand interaction either competitively or allosterically), a BDNF or an NT-4/5 structural analog devoid of agonist activity, a dominant-negative mutation of a trkB receptor that binds BDNF and/or NT-4/5, a trkB immunoadhesin, an anti-trkB antibody, and a trkB inhibitory compound.

In some embodiments, a trkB antagonist (e.g., an antibody) binds (physically interact with) BDNF or NT-4/5, and reduces (impedes and/or blocks) downstream trkB receptor signaling. In some embodiments, a trkB antagonist (e.g., an antibody) binds (physically interact with) trkB receptor, and reduces (impedes and/or blocks) downstream trkB receptor signaling. In some embodiments, a trkB antagonist reduces (impedes and/or blocks) downstream trkB receptor signaling (e.g., inhibitors of kinase signaling). In other embodiments, a trkB antagonist inhibits (reduces) BDNF and/or NT-4/5 synthesis and/or release to the circulation. In some embodiments, the trkB antagonist is a trkB immunoadhesin. In some embodiment, the trkB antagonist binds BDNF (such as hBDNF) and does not significantly bind to related neurotrophins, such as NT-3, NT-4/5, and/or NGF. In some embodiment, the trkB antagonist binds NT-4/5 (such as hNT-4/5) and does not significantly bind to related neurotrophins, such as NT-3, BDNF, and/or NGF. In some embodiments, the trkB antagonist binds both NT-4/5 (such as hNT-4/5) and BDNF (such as hBDNF) but does not significantly bind to related neurotrophins, such as NT-3 and/or NGF. In some embodiments, the trkB antagonist binds a heterodimer of a monomeric NT-4/5 and a monomeric BDNF, but does not significantly bind to related neurotrophins, such as NT-3 and/or NGF. In some embodiments, the trkB antagonist is not associated with an adverse immune response. In some embodiments, the antibody antagonist has impaired effector function. In some embodiments, the small molecule trkB antagonist does not significantly pass blood brain barrier when administered peripherally.

The trkB antagonist may be in the form of a composition for use in any of the methods described herein. The composition used in the methods of the invention comprises an effective amount of a trkB antagonist. The composition can further comprise pharmaceutically acceptable carriers, excipients, or stabilizers (*Remington: The Science and Practice of Pharmacy* 20th Ed. (2000) Lippincott Williams and Wilkins, Ed. K. E. Hoover.), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

TrkB antagonists described herein can be formulated for sustained-release. Suitable examples of sustained-release preparations include semipermeable matrices of solid hydrophobic polymers containing trkB antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid. Another example of sustained release drug-delivery system that can be used is the ATRIGEL® made by Atrix Laboratories. See, for example U.S. Pat. No. 6,565,874. The ATRIGEL® drug delivery system consists of biodegradable polymers, similar to those used in biodegradable sutures, dissolved in biocompatible carriers. TrkB antagonists may be blended into this liquid delivery system at the time of manufacturing or, depending upon the product, may be added later by the physician at the time of use. When the liquid product is injected subcutaneously or intramuscularly through a small gauge needle or placed into accessible tissue sites through a cannula, displacement of the carrier with water in the tissue fluids causes the polymer to precipitate to form a solid film or implant. TrkB antagonists encapsulated within the implant are then released in a controlled manner as the polymer matrix biodegrades with time. Depending upon the patient's medical needs, the Atrigel system can deliver proteins over a period ranging from days to months. Injectable sustained release systems, such as ProLease®, Medisorb®, manufactured by Alkermes may also be used.

In some embodiments, the invention provides compositions (described herein) for use in any of the methods described herein, whether in the context of use as a medicament and/or use for manufacture of a medicament.

The trkB antagonists of this invention may be used in conjunction with other pharmaceutical agents for the treatment of the disease states or conditions described herein. Therefore methods of treatment that include administering compounds of the present invention in combination with other pharmaceutical agents are also provided by the present invention.

Suitable pharmaceutical agents that may be used in combination with the trkB antagonists of the present invention include other anti-obesity agents such as NPYY2 agonists, including PYY, PYY analogs, and PYY derivatives, including pegylated derivatives, cannabinoid-1 (CB-1) antagonists (such as rimonabant), 11β-hydroxy steroid dehydrogenase-1 (11β-HSD type 1) inhibitors, MCR-4 agonists, cholecystokinin-A (CCK-A) agonists, monoamine reuptake inhibitors (such as sibutramine), sympathomimetic agents, β₃ adrenergic receptor agonists, dopamine receptor agonists (such as bromocriptine), melanocyte-stimulating hormone receptor analogs, 5HT2c receptor agonists, melanin concentrating hormone antagonists, leptin, leptin analogs, leptin receptor agonists, galanin antagonists, lipase inhibitors (such as tetrahydrolipstatin, i.e. orlistat), anorectic agents (such as a bombesin agonist), neuropeptide-Y receptor antagonists (e.g., NPY Y5 receptor antagonists), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin receptor antagonists, histamine 3 receptor antagonists or inverse agonists, neuromedin U receptor agonists, MTP/ApoB inhibitors (e.g., gut-selective MTP inhibitors, such as dirlotapide) and the like.

Preferred anti-obesity agents for use in combination with the trkB antagonists of the present invention include CB-1 receptor antagonists, gut-selective MTP inhibitors, CCKa agonists, 5HT2c receptor agonists, NPY Y5 receptor antagonists, orlistat, and sibutramine. Preferred CB-1 receptor antagonists for use in the methods of the present invention include: rimonabant (SR141716A also known under the tradename Acomplia™) is available from Sanofi-Synthelabo or can be prepared as described in U.S. Pat. No. 5,624,941; N-(piperidin-1-yl)-1-(2,4-dichlorophenyl)-5-(4-iodophenyl)-4-methyl-1H-pyrazole-3-carboxamide (AM251) is available from Tocris™, Ellisville, Mo,; [5-(4-bromophenyl)-1-(2,4-dichloro-phenyl)-4-ethyl-N-(1-piperidinyl)-1H-pyrazole-3-carboxamide] (SR147778) which can be prepared as described in U.S. Pat. No. 6,645,985; N-(piperidin-1-yl)-4,5-diphenyl-1-methylimidazole-2-carboxamide, N-(piperidin-1-yl)-4-(2,4-dichlorophenyl)-5-(4-chlorophenyl)-1-methylimidazole-2-carboxamide, N-(piperidin-1-yl)-4,5-di-(4-methylphenyl)-1-methylimidazole-2-carboxamide, N-cyclohexyl-4,5-di-(4-methylphenyl)-1-methylimidazole-2-carboxamide, N-(cyclohexyl)-4-(2,4-dichlorophenyl)-5-(4-chlorophenyl)-1-methylimidazole-2-carboxamide, and N-(phenyl)-4-(2,4-dichlorophenyl)-5-(4-chlorophenyl)-1-methylimidazole-2-carboxamide which can be prepared as described in PCT Pat. Appl. Publ. No. WO 03/075660; the hydrochloride, mesylate and besylate salt of 1-[9-(4-chloro-phenyl)-8-(2-chloro-phenyl)-9H-purin-6-yl]-4-ethylamino-piperidine-4-carboxylic acid amide which can be prepared as described in U.S. Pat. Appl. Publ. No. 2004/0092520; 1-[7-(2-chlorophenyl)-8-(4-chloro-phenyl)-2-methyl-pyrazolo[1,5-a][1,3,5]triazin-4-yl]-3-ethylamino-azetidine-3-carboxylic acid amide and 1-[7-(2-chloro-phenyl)-8-(4-chloro-phenyl)-2-methyl-pyrazolo[1,5-a][1,3,5]triazin-4-yl]-3-methylamino-azetidine-3-carboxylic acid amide which can be prepared as described in U.S. Pat. Appl. Publ. No. 2004/0157839; 3-(4-chloro-phenyl)-2-(2-chloro-phenyl)-6-(2,2-difluoro-propyl)-2,4,5,6-tetrahydro-pyrazolo[3,4-c]pyridin-7-one which can be prepared as described in U.S. Pat. Appl. Publ. No. 2004/0214855; 3-(4-chloro-phenyl)-2-(2-chloro-phenyl)-7-(2,2-difluoro-propyl)-6,7-dihydro-2H,5H-4-oxa-1,2,7-triaza-azulen-8-one which can be prepared as described in U.S. Pat. Appl. Publ. No. 2005/0101592; 2-(2-chloro-phenyl)-6-(2,2,2-trifluoro-ethyl)-3-(4-trifluoromethyl-phenyl)-2, 6-dihydro-pyrazolo[4,3-d]pyrimidin-7-one which can be prepared as described in U.S. Pat. Appl. Publ. No. 2004/0214838; (S)-4-chloro-N-{[3-(4-chloro-phenyl)-4-phenyl-4,5-dihydro-pyrazol-1-yl]-methylamino-methylene}-benzenesulfonamide (SLV-319) and (S)—N-{[3-(4-chloro-phenyl)-4-phenyl-4,5-dihydro-pyrazol-1-yl]-methylamino-methylene}-4-trifluoromethyl-benzenesulfonamide (SLV-326) which can be prepared as described in PCT Pat. Appl. Publ. No. WO 02/076949; N-piperidino-5-(4-bromophenyl)-1-(2,4-dichlorophenyl)-4-ethylpyrazole-3-carboxamide which can be prepared as described in U.S. Pat. No. 6,432,984; 1-[bis-(4-chloro-phenyl)-methyl]-3-[(3,5-difluorophenyl)-methanesulfonyl-methylene]-azetidine which can be prepared as described in U.S. Pat. No. 6,518,264; 2-(5-(trifluoromethyl)pyridin-2-yloxy)-N-(4-(4-chlorophenyl)-3-(3-cyanophenyl)butan-2-yl)-2-methylpropanamide which can be prepared as described in PCT Pat. Appl. Publ. No. WO 04/048317; 4-{[6-methoxy-2-(4-methoxyphenyl)-1-benzofuran-3-yl]carbonyl}benzonitrile (LY-320135) which can be prepared as described in U.S. Pat. No. 5,747,524; 1-[2-(2,4-dichlorophenyl)-2-(4-fluorophenyl)-benzo[1,3]dioxole-5-sulfonyl]-piperidine which can be prepared as described in WO 04/013120; and [3-amino-5-(4-chlorophenyl)-6-(2,4-dichlorophenyl)-furo[2,3-b]pyridin-2-yl]-phenyl-methanone which can be prepared as described in PCT Pat. Appl. Publ. No. WO 04/012671.

Preferred intestinal-acting MTP inhibitors for use in the combinations, pharmaceutical compositions, and methods of the invention include dirlotapide ((S)—N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide) and 1-methyl-5-[(4'-trifluoromethyl-biphenyl-2-carbonyl)-amino]-1H-indole-2-carboxylic acid (carbamoylphenyl-methyl)-amide which can both be prepared using methods described in U.S. Pat. No. 6,720,351; (S)-2-[(4'-trifluoromethyl-biphenyl-2-carbonyl)-amino]-quinoline-6-carboxylic acid (pentylcarbamoyl-phenyl-methyl)-amide, (S)-2-[(4'-tert-butyl-biphenyl-2-carbonyl)-amino]-quinoline-6-carboxylic acid {[(4-fluoro-benzyl)-methyl-carbamoyl]-phenyl-methyl}-amide, and (S)-2-[(4'-tert-butyl-biphenyl-2-carbonyl)-amino]-quinoline-6-carboxylic acid [(4-fluoro-benzylcarbamoyl)-phenyl-methyl]-amide which can all be prepared as described in U.S. Pat. Appl. Publ. No. 2005/0234099A1, (−)-4-[4-[4-[4-[[(2S,4R)-2-(4-chlorophenyl)-2-[[(4-methyl-4H-1,2,4-triazol-3-yl)sulfanyl]methyl-1, 3-dioxolan-4-yl]methoxy]phenyl]piperazin-1-yl]phenyl]-2-(1R)-1-methylpropyl]-2,4-dihydro-3H-1,2,4-triazol-3-one (also known as Mitratapide or R103757) which can be prepared as described in U.S. Pat. Nos. 5,521,186 and 5,929,075; and implitapide (BAY 13-9952) which can be prepared as described in U.S. Pat. No. 6,265,431. Most preferred is dirlotapide, mitratapide, (S)-2-[(4'-trifluoromethyl-biphenyl-2-carbonyl)-amino]-quinoline-6-carboxylic acid (pentylcarbamoyl-phenyl-methyl)-amide, (S)-2-[(4'-tert-butyl-biphenyl-2-carbonyl)-amino]-quinoline-6-carboxylic acid {[(4-fluoro-benzyl)-methyl-carbamoyl]-phenyl-methyl}-amide, or (S)-2-[(4'-tert-butyl-biphenyl-2-carbonyl)-amino]-quinoline-6-carboxylic acid [(4-fluoro-benzylcarbamoyl)-phenyl-methyl]-amide. Preferred NPY Y5 receptor antagonist include: 2-oxo-N-(5-phenylpyrazinyl)spiro[isobenzofuran-1(3H), 4'-piperidine]-1'-carboxamide which can be prepared as described in U.S. Pat. Appl. Publ. No. 2002/0151456; and 3-oxo-N-(5-phenyl-2-pyrazinyl)-spiro[isobenzofuran-1(3H), 4'-piperidine]-1'-carboxamide; 3-oxo-N-(7-trifluoromethylpyrido[3,2-b]pyridin-2-yl)-spiro-[isobenzofuran-1(3H), 4'-piperidine]-1'-carboxamide; N-[5-(3-fluorophenyl)-2-pyrimidinyl]-3-oxospiro-psobenzofuran-1(3H), [4'-piperidine]-1-carboxamide; trans-3'-oxo-N-(5-phenyl-2-pyrimidinyl)]spiro[cyclohexane-1,1'(3'H)-isobenzofuran]-4-carboxamide; trans-3'-oxo-N-[1-(3-quinolyl)-4-imidazolyl]spiro[cyclohexane]-1,1'(3'H)-isobenzofuran]-4-carboxamide; trans-3-oxo-N-(5-phenyl-2-pyrazinyl)spiro[4-azaiso-benzofuran-1(3H), 1'-cyclohexane]-4'-carboxamide; trans-N-[5-(3-fluorophenyl)-2-pyrimidinyl]-3-oxospiro[5-azaisobenzofuran-1(3H), 1'-cyclohexane]-4'-carboxamide; trans-N-[5-(2-fluorophenyl)-2-pyrimidinyl]-3-oxospiro[5-azaisobenzofuran-1(3H), 1'-cyclohexane]-4'-carboxamide; trans-N-[1-(3,5-difluorophenyl)-4-imidazolyl]-3-oxospiro[7-azaisobenzofuran-1 (3H), 1'-cyclohexane]-4'-carboxamide; trans-3-oxo-N-(1-phenyl-4-pyrazolyl)spiro[4-azaisobenzofuran-1(3H), 1'-cyclohexane]-4'-carboxamide; trans-N-[1-(2-fluorophenyl)-3-pyrazolyl]-3-oxospiro[6-azaisobenzofuran-1(3H), 1'-cyclohexane]-4'-carboxamide; trans-3-oxo-N-(1-phenyl-3-pyrazolyl)spiro[6-azaisobenzofuran-1(3H), 1'-cyclohexane]-4'-carboxamide; and trans-3-oxo-N-(2-phenyl-1,2,3-triazol-4-yl)spiro[6-azaisobenzofuran-1(3H), 1'-cyclohexane]-4'-carboxamide, all of which can be prepared as described in described in PCT Pat. Appl. Publ. No. WO 03/082190; and pharmaceutically acceptable salts and esters thereof. All of the above recited U.S. patents and publications are incorporated herein by reference.

Antagonist Antibodies

In some embodiments of the invention, the trkB antagonist comprises an anti-BDNF antibody. An anti-BDNF antibody should exhibit any one or more of the following characteristics: (a) bind to BDNF; (b) inhibit BDNF biological activity or downstream pathways mediated by BDNF signaling function; (c) prevent, ameliorate, or treat any aspect of obesity; (d) block or decrease trkB receptor activation (including trkB receptor dimerization and/or autophosphorylation); (e) increase clearance of circulating BDNF; and (f) inhibit (reduce) BDNF synthesis, production or release.

In some embodiments of the invention, the trkB antagonist comprises an anti-NT-4/5 antibody. An anti-NT-4/5 antibody should exhibit any one or more of the following characteristics: (a) bind to NT-4/5; (b) inhibit NT-4/5 biological activity or downstream pathways mediated by NT-4/5 signaling function; (c) prevent, ameliorate, or treat any aspect of obesity; (d) block or decrease trkB receptor activation (including trkB receptor dimerization and/or autophosphorylation); (e) increase clearance of circulating NT-4/5; and (f) inhibit (reduce) BDNF synthesis, production or release.

In some embodiments of the invention, the trkB antagonist comprises an anti-trkB antibody. An anti-trkB antibody should exhibit any one or more of the following characteristics: (a) bind to the trkB receptor; (b) blocks or inhibits binding of BDNF and/or NT-4/5 to the trkB receptor; (c) inhibit trkB biological activity or downstream pathways mediated by trkB signaling function; (d) prevent, ameliorate, or treat any aspect of obesity; and (e) block or decrease trkB receptor activation (including trkB receptor dimerization and/or autophosphorylation).

The antibodies useful in the present invention can encompass monoclonal antibodies, polyclonal antibodies, antibody fragments (e.g., Fab, Fab', F(ab')$_2$, Fv, Fc, etc.), chimeric antibodies, single chain (ScFv), mutants thereof, fusion proteins comprising an antibody portion, and any other modified configuration of the immunoglobulin molecule that comprises an antigen recognition site of the required specificity. The antibodies may be murine, rat, human, or any other origin (including chimeric or humanized antibodies).

The binding affinity of an antibody to its antigen (such as anti-BDNF antibody to BDNF) may be any of about 500 nM, about 400 nM, about 300 nM, about 200 nM, about 100 nM, about 50 nM, about 10 nM, about 1 nM, about 500 pM, about 100 pM, or about 50 pM to any of about 2 pM, about 5 pM, about 10 pM, about 15 pM, about 20 pM, about 40 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM. As is well known in the art, binding affinity can be expressed as $K_D$, or dissociation constant, and an increased binding affinity corresponds to a decreased $K_D$.

One way of determining binding affinity of antibodies to its antigen is by measuring binding affinity of monofunctional Fab fragments of the antibody. To obtain monofunctional Fab fragments, an antibody (for example, IgG) can be cleaved with papain or expressed recombinantly. The affinity of a Fab fragment of an antibody can be determined by surface plasmon resonance (BIAcore3000™ surface plasmon resonance (SPR) system, BIAcore, INC, Piscaway N.J.). CM5 chips can be activated with N-ethyl-N'-(3-dimethylaminopropyl)-carbodiinide hydrochloride (EDC) and N-hydroxysuccinimide (NHS) according to the supplier's instructions. Antigen (such as BDNF) can be diluted into 10 mM sodium acetate pH 5.0 and injected over the activated chip at a concentration of 0.0005 mg/mL. Using variable flow time across the individual chip channels, two ranges of antigen density can be achieved: 200-400 response units (RU) for detailed kinetic studies and 500-1000 RU for screening assays. The chip can be blocked with ethanolamine. Regeneration studies have shown that a mixture of Pierce elution buffer (Product No. 21004, Pierce Biotechnology, Rockford, Ill.) and 4 M NaCl (2:1) effectively removes the bound Fab while keeping the activity of antigen on the chip for over 200 injections. HBS-EP buffer (0.01M HEPES, pH 7.4, 0.15 NaCl, 3 mM EDTA, 0.005% Surfactant P29) is used as running buffer for the BIAcore assays. Serial dilutions (0.1-10× estimated $K_D$) of purified Fab samples are injected for 1 min at 100 L/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) (generally measured at 25° C.) are obtained simultaneously by fitting the data to a 1:1 Langmuir binding model (Karlsson, R. Roos, H. Fagerstam, L. Petersson, B. (1994). *Methods Enzymology* 6:99-110) using the BIAevaluation program. Equilibrium dissociation constant ($K_D$) values are calculated as $k_{off}/k_{on}$.

In some embodiments, the antibody has impaired effector function. As used herein, an antibody or a polypeptide having an "impaired effector function" (used interchangeably with the term "immunologically inert") refers to antibodies or polypeptides that do not have any effector function or have reduced activity or activities of effector function (compared to antibody or polypeptide having an unmodified or a naturally occurring constant region), e.g., having no activity or reduced activity in any one or more of the following: a) triggering complement mediated lysis; b) stimulating antibody-dependent cell mediated cytotoxicity (ADCC); and c) activating microglia. The effector function activity may be reduced by about any of 10%, 20%, 30%, 40%, 50%, 60%, 70%, 80%, 90%, 95%, 99%, and 100%. In some embodiments, the antibody binds to trkB receptor, BDNF, or NT-4/5 without triggering significant complement dependent lysis, or cell mediated destruction of the target. For example, the Fc receptor binding site on the constant region may be modified or mutated to remove or reduce binding affinity to certain Fc receptors, such as FcγRI, FcγRII, FcγRIII, and/or FcγRIV. For simplicity, reference will be made to antibodies with the understanding that embodiments also apply to polypeptides. EU numbering system (Kabat et al., Sequences of Proteins of Immunological Interest; 5th ed. Public Health Service, National Institutes of Healthy, Bethesda, Md., 1991) is used to indicate which amino acid residue(s) of the constant region (e.g., of an IgG antibody) are altered or mutated. The numbering may be used for a specific type of antibody (e.g., IgG1) or a species (e.g., human) with the understanding that similar changes can be made across types of antibodies and species.

In some embodiments, the antibody comprises a heavy chain constant region having impaired effector function. The heavy chain constant region may have naturally occurring sequence or is a variant. In some embodiments, the amino acid sequence of a naturally occurring heavy chain constant region is mutated, e.g., by amino acid substitution, insertion and/or deletion, whereby the effector function of the constant region is impaired. In some embodiments, the N-glycosylation of the Fc region of a heavy chain constant region may also be changed, e.g., may be removed completely or partially, whereby the effector function of the constant region is impaired.

In some embodiments, the effector function is impaired by removing N-glycosylation of the Fc region (e.g., in the CH 2 domain of IgG). In some embodiments, N-glycosylation of the Fc region is removed by mutating the glycosylated amino acid residue or flanking residues that are part of the glycosylation recognition sequence in the constant region. The tripeptide sequences asparagine-X-serine (N-X-S), asparagine-X-threonine (N-X-T) and asparagine-X-cysteine (N-X-C), where X is any amino acid except proline, are the recognition sequences for enzymatic attachment of the carbohydrate moiety to the asparagine side chain for N-glycosylation. Mutating any of the amino acid in the tripeptide sequences in the constant region yields an aglycosylated IgG. For example, N-glycosylation site N297 of human IgG1 and IgG3 may be mutated to A, D, Q, K, or H. See, Tao et al., *J. Immunology* 143: 2595-2601 (1989); and Jefferis et al., *Immunological Reviews* 163:59-76 (1998). It has been reported that human IgG1 and IgG3 with substitution of Asn-297 with Gln, His, or Lys do not bind to the human FcγRI and do not activate complement with C1q binding ability completely lost for IgG1 and dramatically decreased for IgG3. In some embodiments, the amino acid N in the tripeptide sequences is mutated to any one of amino acid A, C, D, E, F, G, H, I, K, L, M, P, Q, R, S, T, V, W, Y. In some embodiments, the amino acid N in the tripeptide sequences is mutated to a conservative substitution. In some embodiments, the amino acid X in the tripeptide sequences is mutated to proline. In some embodiments, the amino acid S in the tripeptide sequences is mutated to A, D, E, F, G, H, I, K, L, M, N, P, Q, R, V, W, Y. In some embodiments, the amino acid T in the tripeptide sequences is mutated to A, D, E, F, G, H, I, K, L, M, N, P, Q, R, V, W, Y. In some embodiments, the amino acid C in the tripeptide sequences is mutated to A, D, E, F, G, H, I, K, L, M, N, P, Q, R, V, W, Y. In some embodiments, the amino acid following the tripeptide is mutated to P. In some embodiments, the N-glycosylation in the constant region is removed enzymatically (such as N-glycosidase F, endoglycosidase F1, endoglycosidase F2, endoglycosidase F3, and englycosidase H). Removing N-glycosylation may also be achieved by producing the antibody in a cell line having deficiency for N-glycosylation. Wright et al., J Immunol. 160(7):3393-402 (1998).

In some embodiments, amino acid residue interacting with oligosaccharide attached to the N-glycosylation site of the constant region is mutated to reduce binding affinity to FcγRI. For example, F241, V264, D265 of human IgG3 may be mutated. See, Lund et al., *J. Immunology* 157:4963-4969 (1996).

In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000). Antibodies described in PCT WO 99/58572 and Armour et al. comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain has a reduced affinity for FcγRI, FcγRIIa, and FcγRIII. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy. In some embodiments, the heavy chain constant region of the antibody is a human heavy chain IgG1 with any of the following mutations: 1) A327A330P331 to G327S330S331; 2) E233L234L235G236 to P233V234A235 with G236 deleted; 3) E233L234L235 to P233V234A235; 4) E233L234L235G236A327A330P331 to P233V234A235G327S330S331 with G236 deleted; 5) E233L234L235A327A330P331 to P233V234A235G327S330S331; and 6) N297 to A297 or any other amino acid except N. In some embodiments, the heavy chain constant region of the antibody is a human heavy chain IgG2 with the following mutations: A330P331 to S330S331. In some embodiments, the heavy chain constant region of the antibody is a human heavy chain IgG4 with any of the following mutations: E233F234L235G236 to P233V234A235 with G236 deleted; E233F234L235 to P233V234A235; and S228L235 to P228E235.

The constant region of the antibodies may also be modified to impair complement activation. For example, complement activation of IgG antibodies following binding of the C1 component of complement may be reduced by mutating amino acid residues in the constant region in a C1 binding motif (e.g., C1q binding motif). It has been reported that Ala mutation for each of D270, K322, P329, P331 of human IgG1 significantly reduced the ability of the antibody to bind to C1q and activating complement. For murine IgG2b, C1q binding motif constitutes residues E318, K320, and K322. Idusogie et al., *J. Immunology* 164:4178-4184 (2000); Duncan et al., Nature 322: 738-740 (1988).

C1q binding motif E318, K320, and K322 identified for murine IgG2b is believed to be common for other antibody isotypes. Duncan et al., Nature 322: 738-740 (1988). C1q binding activity for IgG2b can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also be possible to use such polar non-ionic residues as Ser, Thr, Cys, and Met in place of residues 320 and 322, but not 318, in order to abolish C1q binding activity.

The invention also provides antibodies having impaired effector function wherein the antibody has a modified hinge region. Binding affinity of human IgG for its Fc receptors can be modulated by modifying the hinge region. Canfield et al., *J. Exp. Med.* 173:1483-1491 (1991); Hezareh et al., *J. Virol.* 75:12161-12168 (2001); Redpath et al., *Human Immunology* 59:720-727 (1998). Specific amino acid residues may be mutated or deleted. The modified hinge region may comprise a complete hinge region derived from an antibody of different antibody class or subclass from that of the CH1 domain. For example, the constant domain (CH1) of a class IgG antibody can be attached to a hinge region of a class IgG4 antibody. Alternatively, the new hinge region may comprise part of a natural hinge or a repeating unit in which each unit in the repeat is derived from a natural hinge region. In some embodiments, the natural hinge region is altered by converting one or more cysteine residues into a neutral residue, such as alanine, or by converting suitably placed residues into cysteine residues. U.S. Pat. No. 5,677,425. Such alterations are carried out using art recognized protein chemistry and, preferably, genetic engineering techniques and as described herein.

Polypeptides that specifically bind to BDNF, NT-4/5 or a trkB receptor and fused to a heavy chain constant region having impaired effector function may also be used for the methods described herein.

Other methods to make antibodies having impaired effector function known in the art may also be used.

Antibodies and polypeptides with modified constant regions can be tested in one or more assays to evaluate level of effector function reduction in biological activity compared to the starting antibody. For example, the ability of the antibody or polypeptide with an altered Fc region to bind complement or Fc receptors (for example, Fc receptors on microglia), or altered hinge region can be assessed using the assays disclosed herein as well as any art recognized assay. PCT WO 99/58572; Armour et al., *Molecular Immunology* 40: 585-593 (2003); Reddy et al., J. Immunology 164:1925-1933 (2000); Song et al., *Infection and Immunity* 70:5177-5184 (2002).

Antibodies may be made by using immunogens, such as BDNF for generating anti-BDNF antibodies, NT-4/5 for generating anti-NT-4/5 antibodies. One example of an immunogen for generating anti-trkB antibodies is cells with high expression of trkB, which can be obtained as described herein. Another example of an immunogen for generating anti-trkB antibodies is a soluble protein (such as a trkB immunoadhesin) which contains the extracellular domain or a portion of the extracellular domain of trkB receptor.

The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells there from can be manipulated to serve as the basis for production of mammalian, including human, hybridoma cell lines. Typically, the host animal is inoculated intraperitoneally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W. at al., (1982) *In Vitro,* 18:377-381. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for the antigen, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human or other species of the immunogen (such as BDNF, NT-4/5, and trkB receptor), or a fragment of the human or other species of the immunogen, or a human or other species of the immunogen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaradehyde, succinic anhydride, $SOCl_2$, or $R1N=C=NR$, where R and R1 are different alkyl groups can yield a population of antibodies (e.g., monoclonal antibodies). Another example of an immunogen for generating anti-trkB antibodies is cells with high expression of trkB, which can be obtained from recombinant means, or by isolating or enriching cells from a natural source that express a high level of trkB. These cells may be of human or other animal origin, and may be used as an immunogen as directly isolated, or may be processed in such that immunogenicity is increased, or trkB expression (of a fragment of trkB) is increased or enriched. Such processing includes, but is not limited to, treatment of the cells or fragments thereof with agents designed to increase their stability or immunogenicity, such as, e.g., formaldehyde, glutaraldehyde, ethanol, acetone, and/or various acids. Further, either before or after such treatment the cells may be processed in order to enrich for the desired immunogen, in this case trkB or fragment thereof. These processing steps can include membrane fractionation techniques, which are well known in the art.

If desired, the antibody (monoclonal or polyclonal) of interest may be sequenced and the polynucleotide sequence may then be cloned into a vector for expression or propagation. The sequence encoding the antibody of interest may be maintained in a vector in a host cell and the host cell can then be expanded and frozen for future use. As an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the antigen. It will be apparent to one of skill in the art that one or more polynucleotide changes can be made to the antibody and still maintain its binding ability to the antigen.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; and 6,548,640. For example, the constant region may be engineered to more resemble human constant regions to avoid immune response if the antibody is used in clinical trials and treatments in humans. See, for example, U.S. Pat. Nos. 5,997,867 and 5,866,692.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. *Nature* 349:293-299 (1991), Lobuglio et al. *Proc. Nat. Acad. Sci. USA* 86:4220-4224 (1989), Shaw et al. *J Immunol.* 138:4534-4538 (1987), and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988), Verhoeyen et al. *Science* 239:1534-1536 (1988), and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert, e.g., does not trigger a complement mediated lysis or does not stimulate antibody-dependent cell mediated cytotoxicity (ADCC). In other embodiments, the constant region is modified as described in *Eur. J. Immunol.* (1999) 29:2613-2624; PCT Application No. PCT/GB99/01441; and/or UK Patent Application No. 9809951.8. Other methods of humanizing antibodies that may also be utilized are disclosed by Daugherty et al., *Nucl. Acids Res.* 19:2471-2476 (1991) and in U.S. Pat. Nos. 6,180,377; 6,054,297; 5,997,867; 5,866,692; 6,210,671; 6,350,861; and PCT Publication No. WO 01/27160. Polyclonal antibodies that can be used as a source for designing appropriate humanized or human anti-BDNF antibodies (e.g., Abcam, Cambridge, Mass., Cat. No. ab6200. Abcam, Cat. No. ab27932; Biosensis, Flagstaff Hill, Australia, Cat. No. R-017-500).

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743 and 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3, 564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primates, equines and bovines.

The antibody may be a bispecific antibody, a monoclonal antibody that has binding specificities for at least two different antigens, can be prepared using the antibodies disclosed herein. Methods for making bispecific antibodies are known in the art (see, e.g., Suresh et al., 1986, *Methods in Enzymology* 121:210). Traditionally, the recombinant production of bispecific antibodies was based on the coexpression of two immunoglobulin heavy chain-light chain pairs, with the two heavy chains having different specificities (Millstein and Cuello, 1983, *Nature* 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; and EP 03089). Heteroconjugate antibodies may be made using any convenient cross-linking methods. Suitable cross-linking agents and techniques are well known in the art, and are described in U.S. Pat. No. 4,676,980.

Antibodies may be made recombinantly by first isolating the antibodies made from host animals, obtaining the gene sequence, and using the gene sequence to express the antibody recombinantly in host cells (e.g., CHO cells). Another method that may be employed is to express the antibody sequence in plants (e.g., tobacco), transgenic milk, or in other organisms. Methods for expressing antibodies recombinantly in plants or milk have been disclosed. See, for example, Peeters et al. (2001) *Vaccine* 19:2756; Lonberg, N. and D. Huszar (1995) *Int. Rev. Immunol* 13:65; and Pollock et al. (1999) *J Immunol Methods* 231:147. Methods for making derivatives of antibodies, e.g., humanized, single chain, etc. are known in the art.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Single chain Fv fragments may also be produced, such as described in Wades et al., 1997, *FEBS Letters*, 409:437-441. Coupling of such single chain fragments using various linkers is described in Kortt et al., 1997, *Protein Engineering*, 10:423-433. A variety of techniques for the recombinant production and manipulation of antibodies are well known in the art.

Antibodies may be modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. Preferably, the effector domain is capable of specifically binding FcRn and/or FcγRIIb. These are typically based on chimeric domains derived from two or more human immunoglobulin heavy chain $C_H2$ domains. Antibodies modified in this manner are preferred for use in chronic antibody therapy, to avoid inflammatory and other adverse reactions to conventional antibody therapy.

The antibodies made either by immunization of a host animal or recombinantly should exhibit any one or more of the trkB antagonist activities described herein.

Immunoassays and flow cytometry sorting techniques such as fluorescence activated cell sorting (FACS) can also be employed to isolate antibodies that are specific for the antigen (such as BDNF, NT-4/5, and a trkB receptor).

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

DNA encoding antagonist antibodies may be sequenced, as is known in the art. Generally, the monoclonal antibody is readily isolated and sequenced using conventional procedures (e.g., by using oligonucleotide probes that are capable of binding specifically to genes encoding the heavy and light chains of the monoclonal antibodies). The hybridoma cells serve as a preferred source of such cDNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., *Proc. Nat. Acad. Sci.* 81: 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of the antigen. The DNA encoding the antagonist antibody (such as an antigen binding fragment thereof) may also be used for delivery and expression of the antibody in a desired cell. DNA delivery techniques are known in the art.

TrkB Immunoadhesins

In some embodiments, the trkB antagonist comprises at least one trkB immunoadhesin. TrkB immunoadhesins as used herein refer to soluble chimeric molecules comprising the extracellular domain of a trkB receptor and an immunoglobulin sequence, which retains the binding specificity of the trkB receptor (substantially retains the binding specificity of the trkB receptor) and is capable of binding to BDNF and/or NT-4/5 (see, e.g., R&D Systems, Minneapolis, Minn., cat no. 688-TK)

TrkB immunoadhesins are known in the art, and have been found to block the binding of BDNF and NT-4/5 to the trkB receptor. See, e.g., U.S. Pat. No. 6,153,189. In one embodiment, the trkB immunoadhesin comprises a fusion of a trkB receptor amino acid sequence (or a portion thereof) from trkB extracellular domain capable of binding BDNF and/or NT-4/5 (in some embodiments, an amino acid sequence that substantially retains the binding specificity of the trkB receptor) and an immunoglobulin sequence. In some embodiments, the trkB receptor is a human trkB receptor sequence, and the fusion is with an immunoglobulin constant domain sequence. In other embodiments, the immunoglobulin constant domain sequence is an immunoglobulin heavy chain constant domain sequence. In other embodiments, the association of two trkB receptor-immunoglobulin heavy chain fusions (e.g., via covalent linkage by disulfide bond(s)) results in a homodimeric immunoglobulin-like structure. An immunoglobulin light chain can further be associated with one or both of the trkB receptor-immunoglobulin chimeras in the disulfide-bonded dimer to yield a homotrimeric or homotetrameric structure. Examples of suitable trkB immunoadhesins include those described in U.S. Pat. No. 6,153,189.

Identification of trkB Antagonists

TrkB antagonists can be identified or characterized using methods known in the art, whereby reduction, amelioration, or neutralization of a trkB biological activity is detected and/or measured. For example, a kinase receptor activation (KIRA) assay described in U.S. Pat. Nos. 5,766,863 and 5,891,650, and in Example 1 can be used to identify trkB antagonists. This ELISA-type assay is suitable for qualitative or quantitative measurement of kinase activation by measuring the autophosphorylation of the kinase domain of a receptor protein tyrosine kinase (hereinafter "rPTK"), e.g. trkB receptor, as well as for identification and characterization of potential antagonists of a selected rPTK, e.g., trkB. The first stage of the assay involves phosphorylation of the kinase domain of a kinase receptor, for example, a trkB receptor, wherein the receptor is present in the cell membrane of an eukaryotic cell. The receptor may be an endogenous receptor or nucleic acid encoding the receptor, or a receptor construct, may be transformed into the cell. Typically, a first solid phase (e.g., a well of a first assay plate) is coated with a substantially homogeneous population of such cells (usually a mammalian cell line) so that the cells adhere to the solid phase. Often, the cells are adherent and thereby adhere naturally to the first solid phase. If a "receptor construct" is used, it usually comprises a fusion of a kinase receptor and a flag polypeptide. The flag polypeptide is recognized by the capture agent, often a capture antibody, in the ELISA part of the assay. An analyte, such as a candidate anti-BDNF antibody or other trkB antagonists, is then added together with BDNF (or NT-4/5 if for identifying anti-NT-4/5 antibody) to the wells having the adherent cells, such that the tyrosine kinase receptor (trkB receptor) is exposed to (or contacted with) BDNF and the analyte. This assay enables identification of antibodies (or other trkB antagonists) that inhibit activation of trkB by its ligand BDNF. Following exposure to BDNF and the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then ready to be subjected to the ELISA stage of the assay. As a first step in the ELISA stage, a second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In one embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

The trkB antagonists can also be identified by incubating a candidate agent with BDNF or NT-4/5 and monitoring any one or more of the following characteristics: (a) binding to BDNF and/or NT-4/5; (b) binding to a trkB receptor; (c) inhibiting trkB biological activity or downstream pathways mediated by trkB signaling function; (d) inhibiting, blocking or decreasing trkB receptor activation (including trkB dimerization and/or autophosphorylation); (e) increasing clearance of circulating BDNF and/or NT-4/5; (f) treating or preventing any aspect of obesity; and (g) inhibiting (reducing) synthesis, production or release of circulating BDNF and/or NT-4/5. In some embodiments, a trkB antagonist is identified by incubating an candidate agent with BDNF or NT-4/5 and monitoring binding and attendant reduction or neutralization of a biological activity of trkB. The binding assay may be performed with purified BDNF or NT-4/5 polypeptide(s), or with cells naturally expressing, or transfected to express, BDNF or NT-4/5 polypeptide(s). In one embodiment, the binding assay is a competitive binding assay, where the ability of a candidate antibody to compete with a known trkB antagonist for BDNF or NT-4/5 binding is evaluated. The assay may be performed in various formats, including the ELISA format. In other embodiments, a trkB antagonist is identified by incubating a candidate agent with BDNF or NT-4/5 and monitoring attendant inhibition of trkB receptor dimerization and/or autophosphorylation.

Following initial identification, the activity of a candidate trkB antagonist can be further confirmed and refined by bioassays, known to test the targeted biological activities. Alternatively, bioassays can be used to screen candidates directly. For example, BDNF and NT-4/5 promotes a number of morphologically recognizable changes in responsive cells. Thus, the assay for inhibition of trkB biological activity entail culturing BDNF and/or NT-4/5 responsive cells with BDNF or NT-4/5 plus an analyte, such as a candidate anti-BDNF antibody, a candidate anti-NT-4/5 antibody, and a candidate trkB antagonist. After an appropriate time the cell response will be assayed (cell differentiation, neurite outgrowth or cell survival). For example, a candidate antagonist can be tested in the PC12 neurite outgrowth assay using PC12 cells transfected with full-length trkB. Jian et al., Cell Signal. 8:365-70, 1996.

The ability of a candidate trkB antagonist to block or neutralize a biological activity of trkB can also be assessed by monitoring the ability of the candidate agent to inhibit BDNF or NT-4/5 mediated survival in the embryonic mouse nodose ganglion neurons survival bioassay as described in Buchman et al., Development 118:989-1001, 1993.

V. Kits

The invention also provides kits for use in the instant methods. Kits of the invention include one or more containers comprising a purified trkB antagonist (for example, an anti-BDNF antagonist antibody, an anti-NT-4/5 antagonist antibody, and an anti-trkB antagonist antibody) and instructions for use in accordance with any of the methods of the invention described herein. Generally, these instructions comprise a description of administration of the trkB antagonist to treat a disease, such as obesity, according to any of the methods described herein. The kit may further comprise a description of selecting an individual suitable for treatment based on identifying whether that individual has the disease and the stage of the disease.

The instructions relating to the use of trkB antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating a disease described herein (such as obesity). Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a trkB antagonist. The container may further comprise a second pharmaceutically active agent.

Kits may optionally provide additional components such as buffers and interpretive information. Normally, the kit comprises a container and a label or package insert(s) on or associated with the container.

The following examples are provided to illustrate, but not to limit, the invention.

EXAMPLES

Example 1

Generation and Screening of Anti-BDNF Antibodies

Immunization for generating monoclonal anti-BDNF antagonist antibodies: A single Balb/C mouse was injected 5 times on a regular schedule with 25 ug of human BDNF as antigen. Human BDNF was obtained from Prepro Tech Inc. (Rocky Hill, N.J.). For the first 4 injections, antigen was prepared by mixing human BDNF with RIBI adjuvant system and alum. Twenty five ug total of antigen was given via injection to the scruff of the neck, the foot pads and IP, approximately every 3 days over the course of 11 days. On Day 13, the mouse was euthanized and the spleen was removed. Lymphocytes were fused with 8653 cells to make hybridoma clones. Clones were allowed to grow then selected as anti-BDNF positives by ELISA screening with Human BDNF ELISA.

ELISA screening anti-BDNF antibodies: Supernatants from growing hybridoma clones were screened for their ability to bind human BDNF. The assays were performed with 96-well plates coated overnight with 100 ul of 0.5 ug/ml human BDNF. Excess reagents are washed from the wells between each step with PBS containing 0.05% Tween-20. Plates were then blocked with phosphate buffered saline (PBS) containing 0.5% BSA. Supernatant was added to the plates and incubated at room temperature for 2 hours. Horse radish peroxidase (HRP) conjugated goat-anti mouse Fc was added to bind to the mouse antibodies bound to human BDNF. Tetramethyl benzidine was then added as substrate for HRP to detect amount of mouse antibody present in the supernatant. The reaction was stopped and the relative amount of antibody was quantified by reading the absorbance at 450 nm. One antibody 1B5 was identified to bind to human BDNF and was further tested for antagonist activity in KIRA assay.

Human TrkB blocking KIRA Assay: This assay was used to screen antibodies found positive in the ELISA for the ability to block receptor tyrosine kinase activation for human trkB. See Sadick et. al., 1997, Experimental Cell Research, 234(2):354-61. Utilizing a stable cell line transfected with gD tagged human trkB, purified murine antibodies from the hybridoma clones were tested for their ability to block the activation of the trkB receptor on the surface of the cells in the presence of BDNF. An efficient blocking antibody would show reduced tyrosine phosphorylation of trkB and can be performed in a dose dependent manner. Natural ligand induced self phosphorylation of the kinase domain of the trkB receptor. After the cells were exposed to the mixture of a defined concentration of BDNF and antibodies in the form of 20% of hybridoma supernatant (i.e., the mixture contains 20% (vol/vol) hybridoma supernatant), they were lysed and an ELISA was performed to detect phosphorylation of the trkB receptor. Using this assay, antibody 1B5 was shown to block trkB activation by BDNF (FIG. 1). FIG. 1 shows the trkB tyrosine phosphorylation dose response to BDNF in the presence or the absence of 1B5 anti-BDNF antibody. The data indicated that the trkB tyrosine phosphorylation induced by BDNF was significantly reduced by the presence of 1B5 antibody supernatant.

E18 Nodose neuron survival assay: The Nodose ganglion neurons obtained from E18 embryos were supported by BDNF, so that at saturating concentrations of the neurotrophic factor the survival was close to 100% (i.e. 200-250 neurons) by 48 hours in culture. In the absence of BDNF, about 40-50% of the neurons (i.e. 90-100 neurons) survived by 48 hours. Therefore, the survival of E18 nodose neurons is a sensitive assay to evaluate the blocking activity of anti-BDNF antibodies, i.e. the blocking antibodies will reduce survival of E18 nodose neurons in the presence of a constant and saturating level of BDNF.

Time-mated pregnant CD-1 female mice were euthanized by $CO_2$ inhalation. The uterine horns were removed and the embryos at embryonic stage E18 were extracted. The nodose ganglia were dissected then trypsinized, mechanically dissociated and plated at a density of 200-300 cells per well in defined, serum-free medium in 96-well plates coated with poly-L-ornithine and laminin. The blocking activity of anti-BDNF antibodies was evaluated in a dose-response manner in triplicates in the presence of constant level of BDNF (0.5 ng/mL). After 48 hours in culture the cells were subjected to an automated immunocytochemistry protocol performed on a Biomek FX liquid handling workstation (Beckman Coulter). The protocol included fixation (4% formaldehyde, 5% sucrose, PBS), permeabilization (0.3% Triton X-100 in PBS), blocking of unspecific binding sites (5% normal goat serum, o.1% BSA, PBS) and sequential incubation with a primary and secondary antibodies to detect neurons. A rabbit polyclonal antibody against the protein gene product 9.5 (PGP9.5, Chemicon), which was an established neuronal phenotypic marker, was used as primary antibody. Alexa Fluor 488 goat anti-rabbit (Molecular Probes) was used as secondary reagent together with the nuclear dye Hoechst 33342 (Molecular Probes) to label the nuclei of all the cells present in the culture. Image acquisition and image analysis were performed on a Discovery-1/GenII Imager (Universal Imaging Corporation). Images were automatically acquired at two wavelengths for Alexa Fluor 488 and Hoechst 33342, with the nuclear staining being used as reference point, since it is present in all the wells, for the image-based auto focus-system of the Imager. Appropriate objectives and number of sites imaged per well were selected to cover the entire surface of each well. Automated image analysis was set up to count the number of neurons present in each well after 48 hours in culture based on their specific staining with the anti-PGP9.5 antibody. Careful thresholding of the image and application of morphology and fluorescence intensity based selectivity filters resulted in an accurate count of neurons per well.

FIG. 2A is a graph of the nodose neuron survival dose response to BDNF alone. The data indicated that maximal number of neuron survival was obtained with BDNF from 0.1-0.5 ng/ml. FIG. 2B is a graph of the nodose neuron survival in the presence of saturating concentration (0.5 ng/mL) of BDNF and increasing concentrations of 1B5 anti-BDNF antibody. The data indicated that at extremely high concentration of 1B5 antibody, the level of nodose neuronal survival was approximating that in the absence of BDNF (close to 100 neurons surviving at 48 hours). The 50% effective blocking concentration (EC50) of 1B5 antibody under this condition was about 0.4-1 nM.

Example 2

Peripheral Injection of Anti-BDNF Antibody (1B5) Reduced Body Weight and Food Intake in High Fat Diet Induced Obese (DIO) Mice Test animals: C57BL/6 male mice with diet induced obesity (DIO) from Jackson Laboratory were used in this study. El-Haschimi, J. Clin. Invest. 105:1827-1832 (2000); Steppan, Nature 409:307-312 (2001). Twenty four male C57BL/6J mice were weaned at 4 weeks of age. Immediately after weaning they were put on about 60% high fat diet (D12331i, Research Diet) through out the study. The DIO mice at 13 weeks of age weighing in the range of 28-40 g were used in this study. These mice were housed in a temperature (19.5-24.5° C.) and relative humidity (45-65%) controlled room with a 12-hour light/dark cycle, with ad libitum access to filtered tap-water and 60% high fat diet (D12331i, Research Diet) throughout the study. Upon receipt at animal facilities, they were housed 1 per cage covered with filtered caps and at least a 5-day acclimation period was observed.

Administration of anti-BDNF 1B5 and NT-4/5: The mice were divided into 3 groups of equivalent body weight (n=8 for each group). Each group received on day 1 a subcutaneous dose of either vehicle, 5 mg/kg of human NT-4/5, or 5 mg/kg of anti-BDNF antibody 1B5, respectively. Body weight (measured before treatment) and food intake were measure on day 1 and on day 2.

As shown in FIG. 3A and FIG. 3B, both NT-4/5 and anti-BDNF significantly reduced body weight (FIG. 3A) and food intake (FIG. 3B). Two way ANOVA and Bonferroni post-tests were used for statistical analysis. "" indicates $P<0.01$; and "*" indicates $P<0.001$ for treatment group compared to the vehicle control group.

Example 3

Peripheral Injection of Antagonist trkB-Fc Fusion Protein Reduced Body Weight and Food Intake in Cynomolgus Monkeys Adult male and female cynomolgus monkeys (weighing 4-5 kg at baseline) were acclimated to high fat monkey diet for 60 days before entering into this study. Three animals (2 females and 1 male) received intravenously injections of recombinant human trkB-Fc fusion protein and the other three animals (2 females and 1 male) received vehicle twice a week from day 1 to day 35. Food consumption was monitored daily. The body weight and length were monitored weekly, and BMI was calculated by the formula BMI=(body weight in kg)/(length in meters)$^2$. The statistical analyses were performed by using PRISM (GraphPad Software Inc., San Diego, Calif.). All data and graphs were expressed in mean±standard error of mean (SEM).

The monkeys that were treated twice a week with IV injections of 5 mg/kg of the trkB-Fc protein exhibited a trend toward decrease in food intake within 2 weeks of treatment (FIG. 1A) and significant decrease in body mass index BMI (FIG. 1B) by day 30 after treatment started ($P \approx 0.0083$, $F \approx 8.285$, 2-way ANOVA). These data indicate that using a trkB antagonist, such as a soluble trkB-Fc fusion protein, results in reduction of food intake and body weight.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

What is claimed is:

1. A method for treating obesity or a condition of being overweight in a mammal in need of such treatment, comprising peripherally administering to the mammal a therapeutically effective amount of a trkB antagonist or a pharmaceutically acceptable salt thereof, wherein the trkB antagonist is an anti-BDNF antibody, an anti-trkB antagonist antibody, or a trkB-Fc fusion protein comprising the extracellular domain of a naturally-occurring mammalian trkB receptor.

2. The method of claim 1, wherein the trkB antagonist is an anti-BDNF antibody.

3. The method of claim 1, wherein the trkB antagonist is an anti-trkB antagonist antibody.

4. The method of claim 1, wherein the trkB antagonist is a trkB-Fc fusion protein comprising the extracellular domain of a naturally-occurring mammalian trkB receptor.

5. The method of claim 1, wherein the mammal is a human.

6. A method of inhibiting weight gain, reducing food intake or reducing caloric intake in a mammal in need of such treatment, comprising peripherally administering to the mammal a therapeutically effective amount of a trkB antagonist or a pharmaceutically acceptable salt thereof, wherein the trkB antagonist is an anti-BDNF antibody, an anti-trkB antagonist antibody, or a trkB-Fc fusion protein comprising the extracellular domain of a naturally-occurring mammalian trkB receptor.

7. The method of claim 6, wherein the trkB antagonist is an anti-BDNF antibody.

8. The method of claim 6, wherein the trkB antagonist is an anti-trkB antagonist antibody.

9. The method of claim 6, wherein the trkB antagonist is a trkB-Fc fusion protein comprising the extracellular domain of a naturally-occurring mammalian trkB receptor.

10. The method of claim 6, wherein the mammal is a human.

11. The method of any one of claims 1-10, wherein the trkB antagonist or pharmaceutically acceptable salt thereof is administered in combination with a second agent that is an anti-obesity agent.

12. The method of claim 3 or 8, wherein the anti-trkB antagonist antibody is bound to a carrier.

13. The method of claim 12, wherein the carrier is selected from a group consisting of polypropylene, polystyrene, polyethylene, dextran, nylon, amylases, glass, natural and modified celluloses, polyacrylamides, agaroses and magnetite.

* * * * *